(12) United States Patent
Virag et al.

(10) Patent No.: US 8,812,107 B2
(45) Date of Patent: *Aug. 19, 2014

(54) TERMINATING TACHYARRHYTHMIAS

(75) Inventors: Nathalie Virag, Cottens (CH); Laurent Uldry, Martigny (CH); Fredric W. Lindemans, Sittard (NL); Lukas J. Kappenberger, Lausanne (CH)

(73) Assignee: Medtronic, Inc., Minneapolis, MN (US)

( * ) Notice: Subject to any disclaimer, the term of this patent is extended or adjusted under 35 U.S.C. 154(b) by 328 days.

This patent is subject to a terminal disclaimer.

(21) Appl. No.: 12/826,010

(22) Filed: Jun. 29, 2010

(65) Prior Publication Data

US 2011/0319952 A1    Dec. 29, 2011

(51) Int. Cl.
 *A61N 1/365* (2006.01)
(52) U.S. Cl.
 USPC .......................................................... 607/14
(58) Field of Classification Search
 USPC .......................................................... 607/14
 See application file for complete search history.

(56) References Cited

U.S. PATENT DOCUMENTS

| | | | |
|---|---|---|---|
| 4,284,082 A | 8/1981 | Funke et al. | |
| 5,203,326 A | 4/1993 | Collins | |
| 5,243,978 A | 9/1993 | Duffin, Jr. | |
| 5,683,429 A | 11/1997 | Mehra | |
| 5,855,592 A | 1/1999 | McGee et al. | |
| 6,085,116 A | 7/2000 | Pendekanti et al. | |
| 6,337,995 B1 | 1/2002 | Mower | |
| 6,654,639 B1 * | 11/2003 | Lu | 607/17 |
| 6,662,045 B2 | 12/2003 | Zheng et al. | |
| 6,829,504 B1 * | 12/2004 | Chen et al. | 607/4 |
| 7,006,867 B1 * | 2/2006 | Kroll | 607/14 |
| 7,225,020 B1 | 5/2007 | Kroll et al. | |
| 7,363,081 B1 | 4/2008 | Kroll et al. | |
| 8,086,307 B2 * | 12/2011 | Virag et al. | 607/5 |
| 2003/0208241 A1 | 11/2003 | Bradley et al. | |

FOREIGN PATENT DOCUMENTS

WO     0222207 A1    3/2002
WO  2011014279 A1    2/2011

OTHER PUBLICATIONS

Kale et al., "Atrial septal pacing in the prevention of paroxysmal atrial fibrillation refractory to antiarrhythmic drugs," International Journal of Cardiology 82(2):167-175, Feb. 2002.

Redfearn et al., "Pacing delivered rate and rhythm control for atrial fibrillation," Current Opinion in Cardiology, Mar. 2006, vol. 21, Issue 2, pp. 83-87.

Ellenbogen, "Pacing therapy for prevention of atrial fibrillation," Heart Rhythm, Mar. 2007, vol. 4, Issue 3, Supplement, pp. S84-S87.

Misier et al., "Multi-site atrial pacing: an option for atrial fibrillation prevention? Preliminary results of the dutch dual-site right atrial pacing for prevention of atrial fibrillation study," American Journal of Cardiology, vol. 86, No. 9, Nov. 2, 2000, Supplement 1, pp. 20K-24K.

(Continued)

*Primary Examiner* — Eric D. Bertram
(74) *Attorney, Agent, or Firm* — Michael C. Soldner

(57) ABSTRACT

This disclosure is directed to techniques for treating tachyarrhythmias, such as atrial or ventricular fibrillation, in which a number of electrodes are employed to deliver electrical stimulation to a patient's heart in a manner designed to terminate the tachyarrhythmia episode.

19 Claims, 14 Drawing Sheets

(56) References Cited

OTHER PUBLICATIONS

Hansen et al., "High-density biatrial pacing protects against atrial fibrillation by synchronizing left atrial tissue," Journal of Interventional Cardiac Electrophysiology, vol. 27, No. 2, Dec. 9, 2009, DOI 10.1007/s10840-009-9453-0, pp. 81-87.
Spencer et al., "Atrial septal pacing: A method for pacing both atria simultaneously," Pacing and Clinical Electrophysiology, Nov. 1997, vol. 20, Issue 11, pp. 2739-2745.
Padeletti et al., "Atrial septal pacing: A new approach to prevent atrial fibrillation," Pacing and Clinical Electrophysiology, Jun. 2004, vol. 27, Issue 6 (Pt.II), pp. 850-854.
Becker et al., "Suppression of atrial fibrillation by multisite and septal pacing in a novel experimental model," Cardiovascular Research, 2002, vol. 54, Issue 2, pp. 476-481.
Hermida et al., "Atrial septal pacing to prevent atrial fibrillation in patients with sinus node dysfunction: Results of a randomized controlled study," American Heart Journal, Aug. 2004, vol. 148, Issue 2, pp. 312-317.
Hakacova et al., "Septal atrial pacing for the prevention of atrial fibrillation," Europace, 2007, vol. 9, Issue 12, pp. 1124-1128.
Padeletti et al., "Combined efficacy of atrial septal lead placement and atrial pacing algorithms for prevention of paroxysmal atrial tachyarrhythmia," Journal of Cardiovascular Electrophysiology, Nov. 2003, vol. 14, No. 11, pp. 1189-1195.
Lau et al., "A prospective randomized study to assess the efficacy of rate and site of atrial pacing on long-term development of atrial fibrillation," Journal of Cardiovascular Electrophysiology, Sep. 2009, vol. 20, Issue 9, pp. 1020-1025.
Uldry et al., "Optimizing Local Capture of Atrial Fibrillation by Rapid Pacing: Study of the Influence of Tissue Dynamics," Annals of Biomedical Engineering, vol. 38, No. 12, Dec. 2010, pp. 3664-3673.
Virag et al., "Study of atrial arrhythmias in a computer model based on magnetic resonance images of human atria," Chaos: An Interdisciplinary Journal of Nonlinear Science, Sep. 2002, vol. 12, Issue 3, pp. 754-763.
Jacquemet et al., "Wavelength and vulnerability to atrial fibrillation: Insights from a computer model of human atria," Europace, Jul. 28, 2005, vol. 7, Supplement 2, pp. S83-S92.
Luo et al., "A model of ventricular cardiac action potential," Circulation Research, Jun. 1991, vol. 68, No. 6, pp. 1501-1526.
Kim et al., "Action potential duration restitution kinetics in human atrial fibrillation," Journal of the American College of Cardiology, Apr. 17, 2002, vol. 39, No. 8, pp. 1329-1336.
Gillis et al., "High atrial antitachycardia pacing therapy efficacy is associated with a reduction in atrial tachyarrythmia burden in a subset of patients with sinus node dysfunction and paroxysmal atrial fibrillation," Heart Rhythm, May 26, 2005, vol. 2, Issue 8, pp. 791-796.
Gulizia et al., "Randomized comparison between Ramp and Burst+ atrial antitachycardia pacing therapies in patients suffering from sinus node disease and atrial fibrillation and implanted with a DDDRP device," Europace, Mar. 19, 2006, vol. 8, Issue 7, pp. 465-473.
Janko et al., "Atrial antitachycardia pacing: do we still need to talk about it?" Europace, Jul. 9, 2009, vol. 11, Issue 8, pp. 977-979.
Fenton et al., "Termination of atrial fibrillation using pulsed low-energy far-field stimulation," Circulation, Aug. 11, 2009, vol. 120, Issue 6, pp. 467-476.
Duytschaever et al., "Methods for determining the refractory period and excitable gap during persistent atrial fibrillation in the goat," Circulation, Aug. 21, 2001, vol. 104, Issue 8, pp. 957-962.
Tanaka et al., "Unpinning of spiral wave anchored around a circular obstacle by an external wave train: common aspects of a chemical reaction and cardiomyocyte tissue," Chaos: An Interdisciplinary Journal of Nonlinear Science, Nov. 19, 2009, vol. 19, Issue 4, 043114, 5 pp.
U.S. Appl. No. 12/533,650, by Nathalie Virag, filed Jul. 31, 2009.
International Search Report and Written Opinion of international application No. PCT/US2011/033995, dated Aug. 25, 2011, 12 pp.
International Preliminary Report on Patentability from corresponding PCT Application Serial No. PCT/US2011/033995 dated Jan. 17, 2013 (9 pages).

* cited by examiner

TERMINATING TACHYARRHYTHMIAS

This application is related to U.S. application Ser. No. 12/533,650, filed Jul. 31, 2009, the entire content of which is incorporated herein by this reference.

TECHNICAL FIELD

The invention generally relates to implantable medical devices (IMD's) including pacemakers for detecting and treating cardiac arrhythmias, and more particularly to techniques employed by IMD's for monitoring and treating atrial tachyarrhythmias, such as atrial fibrillation.

BACKGROUND

When functioning properly, a heart maintains its own intrinsic rhythm, and is capable of pumping adequate blood throughout a circulatory system. This intrinsic rhythm is a function of electrical signals generated by the sinoatrial node, or SA node, located in the upper right atrium of the heart. The SA node periodically depolarizes, which in turn causes the atrial heart tissue to depolarize such that right and left atria contract as the depolarization travels through the atrial heart tissue. The atrial depolarization signal is also received by the atrioventricular node, or AV node, which, in turn, triggers a subsequent ventricular depolarization signal that travels through and depolarizes the ventricular heart tissue causing the right and left ventricles to contract.

Some patients, however, have irregular cardiac rhythms, referred to as cardiac arrhythmias. An arrhythmia, in general, is a disturbance in the normal rate, rhythm or conduction pattern of the heart. Cardiac arrhythmias may result in diminished blood circulation because of diminished cardiac output. Atrial fibrillation is the most common cardiac arrhythmia and it reduces the pumping efficiency of the heart. Atrial fibrillation is characterized by rapid, irregular, uncoordinated activation waves conducting in various directions over the atria that, as a result, do not produce a coordinated, effective contraction. Without atrial contraction, the ventricles are less optimally filled before their contraction, which may lead to a reduced cardiac output. This reduced pumping efficiency due to atrial fibrillation requires the ventricle to work harder, which is particularly undesirable in sick patients who cannot tolerate additional stress. Although atrial fibrillation episodes are generally not life-threatening, they may be associated with extreme symptoms, a reduced quality of life, a reduced cardiac output and unpleasantly rapid and irregular heart rates being felt by the patient. Due to the lack of atrial contraction during atrial fibrillation, clots may form in the stagnant blood in the atria which, if they dislodge from the left atrial endocardium, may occlude small arteries in the brain or other organs, causing stroke. This is why patients with atrial fibrillation must take anticoagulant therapy.

For heart patients having a multi-chamber pacemaker, atrial fibrillation episodes present an additional problem, in that the pacemaker may coordinate ventricular pacing with atrial activity. When an atrial fibrillation episode begins, it is undesirable for ventricular pacing to be timed according to this pathological atrial activity. Accordingly, some pacemakers are equipped with "mode switching" capability that automatically switches to a non-tracking mode, such as DDIR, when atrial fibrillation is detected.

In patients with an implantable cardioverter defibrillator, atrial fibrillation may cause such high ventricular rates that the device incorrectly delivers therapy for ventricular tachycardia or fibrillation which can be very unpleasant for the patient. Additionally, in patients with heart failure and an implanted cardiac resynchronization device, the occurrence of atrial fibrillation not only compromises cardiac output because the ventricles are no longer optimally filled by atrial contractions, but present resynchronization devices loose effectiveness when they cannot synchronize to a regular atrial activation.

When an atrial fibrillation episode occurs, the pacemaker or another medical device may apply therapy to attempt to terminate the irregular arrhythmia. Therapy may include applying a shock or delivering a drug. While maintaining a high heart rate has been demonstrated to reduce the incidence of atrial fibrillation episodes in some patients (overdrive pacing), only defibrillation shocks are effective to terminate an ongoing atrial fibrillation episode. Anti-tachy pacing therapies may terminate episodes of atrial flutter (a regular but overly fast atrial rhythm) but have not been demonstrated to terminate atrial fibrillation.

SUMMARY

In general, examples disclosed herein are directed to treating tachyarrhthmias, such as atrial fibrillation, by employing a number of electrodes to deliver electrical stimulation to a patient's heart in a manner designed to terminate a tachyarrhythmia episode.

In one example, a method for terminating a tachyarrhythmia includes detecting the tachyarrhythmia, delivering overdrive pacing to a septum of a heart of a patient in response to the detection, delivering a first underdrive pacing to the septum at a first frequency, and delivering a second underdrive pacing to the septum at a second frequency.

In another example, a system includes an implantable medical lead, a number of electrodes, a signal generator, and a processor. The electrodes are connected to the lead. The lead is configured to arrange the electrodes symmetrically on a septum of a heart of a patient when implanted within the heart. The signal generator is connected to the electrodes by the lead. The processor is configured to control the signal generator to deliver overdrive pacing to the septum, deliver a first underdrive pacing to the septum at a first frequency, and deliver a second underdrive pacing to the septum at a second frequency.

In another example, a method includes delivering overdrive pacing to one or both atria of a heart of a patient followed abruptly by delivering a first underdrive pacing at a first frequency and a second underdrive pacing at a second frequency to the one or both atria of the heart.

In another example, a method for terminating a tachyarrhythmia includes detecting the tachyarrhythmia, delivering overdrive pacing epicardially in a transition zone between a right atrium and a left atrium of a heart of a patient in response to the detection, delivering a first underdrive pacing at a first frequency epicardially to the transition zone, and delivering a second underdrive pacing at a second frequency epicardially to the transition zone.

In another example, a system includes an implantable medical lead, a number of electrodes, a signal generator, and a processor. The electrodes are connected to the lead. The lead is configured to arrange the electrodes on an epicardium of a heart of a patient in a transition zone between a right atrium and a left atrium when implanted within the heart. The signal generator is connected to the electrodes by the lead. The processor is configured to control the signal generator to deliver overdrive pacing to the epicardium in the transition zone, deliver a first underdrive pacing at a first frequency to the epicardium in the transition zone, and deliver a second underdrive pacing at a second frequency to the epicardium in the transition zone.

The details of one or more examples are set forth in the accompanying drawings and the description below. Other features, objects, and advantages will be apparent from the description and drawings, and from the claims.

DETAILED DESCRIPTION

Figure 1:
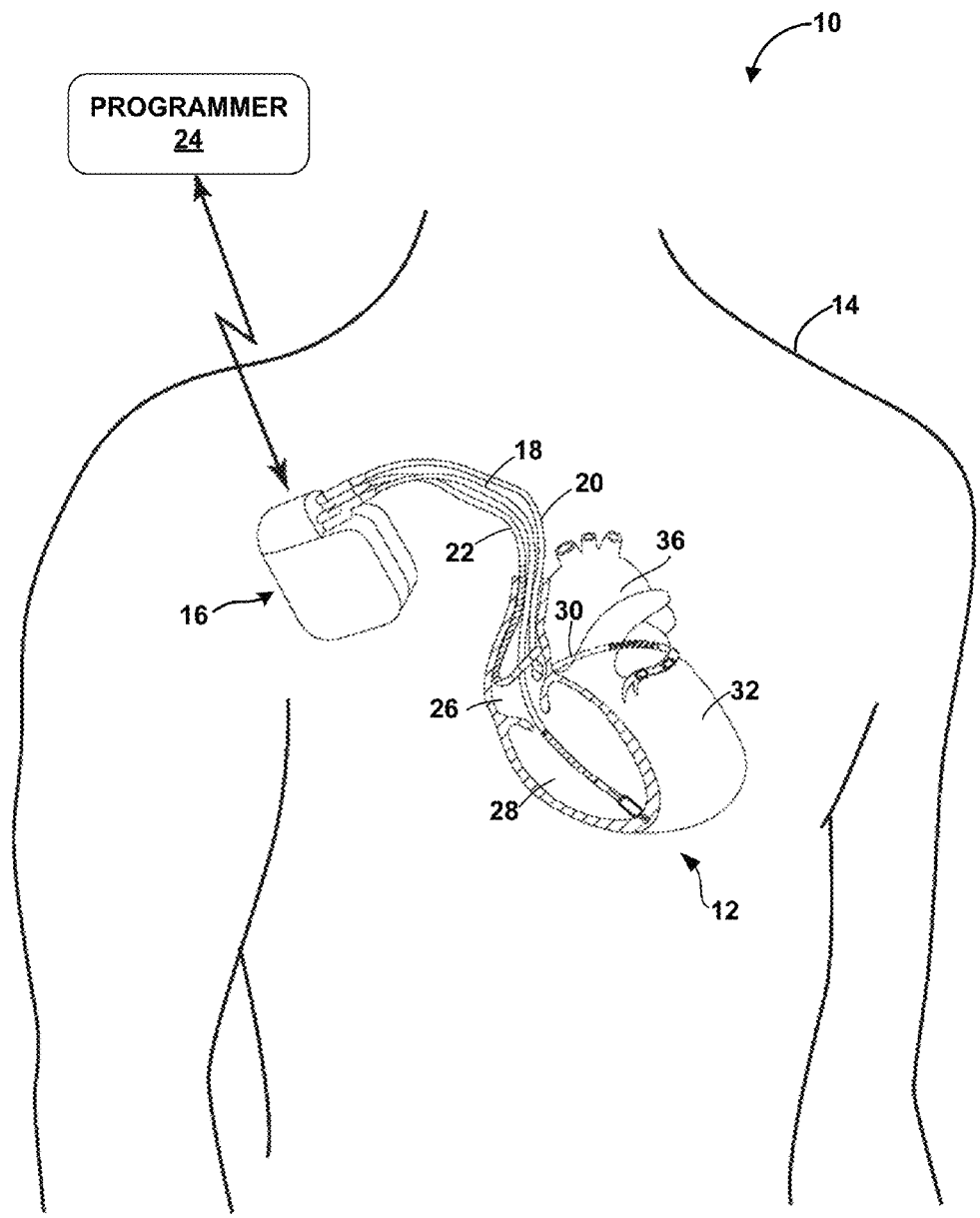
FIG. 1 is a schematic view of an example system including implantable medical device (IMD) configured to detect atrial tachyarrhythmia and deliver electrical stimulation to terminate the atrial tachyarrhythmia.

FIG. 1 is a conceptual diagram illustrating an example therapy system 10 used to monitor one or more physiological parameters of patient 14 and/or to provide therapy to heart 12 of patient 14. Therapy system 10 includes an implantable medical device (IMD) 16, which is coupled to leads 18, 20, and 22, and programmer 24. In some examples, IMD 16 is an implantable pacemaker that provides electrical signals to heart 12 via electrodes coupled to one or more of leads 18, 20, and 22. In some examples, IMD 16 also includes cardioversion, defibrillation, and/or cardiac resynchronization functionalities. Patient 12 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12.

In some examples, LV lead 20 is used in combination with RV lead 18 to deliver biventricular pacing to heart 12, which provides cardiac resynchronization therapy (CRT) to heart 12. CRT may be used to treat heart failure-inducted conduction disturbances and/or ventricular dyssynchrony. In some cases, CRT helps restore the mechanical sequence of ventricular activation and contraction. In some examples, CRT involves biventricular pacing, e.g., via RV lead 18 and LV lead 20, to synchronize the contraction of both ventricles. In other examples, CRT involves pacing one of the ventricles, e.g., LV 32 via LV lead 20, to synchronize its contraction with that of the other ventricle.

Right atrial (RA) lead 22 extends through one or more veins and the vena cava, and into the right atrium 26 of heart 12. RA lead 22 is positioned along the atrial septum that separates right atrium 26 and left atrium 36. In some examples, a portion of RA lead 22 may be positioned in the posterior portion of right atrium 26 around the coronary sinus ostium along the atrial septum. In some examples, RA lead 22 is positioned such that RA lead 22 senses electrical activity within right atrium 26 and left atrium 36, as well as paces right atrium 26 and left atrium 36.

As described in greater detail below, RA lead 22 includes a plurality of electrodes (not shown in FIG. 1) arranged symmetrically on the atrial septum of heart 12 between right atrium 26 and left atrium 36. In some examples, the electrodes are arranged symmetrically about the fossa ovalis on the atrial septum. The electrodes on the atrial septum are configured to produce strong and uniform depolarization waves that propagate symmetrically in both right atrium 26 and left atrium 36 of heart 12. Additionally, IMD 16 includes a processor that is configured to control the electrodes arranged on the atrial septum to deliver overdrive pacing followed abruptly by delivering a first underdrive pacing at a first frequency and then a second underdrive pacing at a second frequency to right atrium 26 and left atrium 36. Delivering overdrive and underdrive pacing, e.g., including the first and then second underdrive pacing, in sequence with an abrupt transition there between may act to inhibit continuation of any fibrillating waves that present during the overdrive pacing. As used herein, an abrupt transition means that there is no pacing frequency transition, e.g. ramping pacing frequency down, between the overdrive and the first underdrive pacing phases employed in the disclosed examples. In general, the transition between overdrive and underdrive pacing is substantially immediate, without delivery of other frequencies or modes or pacing, or without a period in which pacing is not delivered. In some examples, the transition occurs within approximately one cardiac cycle length, e.g., within 0 to 300 milliseconds. Although the disclosed examples are described with reference to a number of electrodes arranged symmetrically on the atrial septum of a patient's heart and, in some examples, in a ring around the fossa ovalis on the atrial septum, in some examples according to this disclosures, the electrodes may be arranged in a number of other configurations on the septum of the heart, including, e.g., arranging the electrodes asymmetrically on the septum.

Generally speaking, IMD 16 senses electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar.

In some examples, IMD 16 triggers ventricular pacing, e.g., RV, LV, or biventricular pacing, based on atrial depolarizations sensed via RA lead 22. As another example, RA lead 22 may deliver atrial pacing, and IMD 16 triggers ventricular pacing based on atrial-paced events. In some examples, RV lead 18 and/or LV lead 20 sense ventricular depolarizations, and IMD 16 triggers ventricular pacing, e.g., RV, LV, or biventricular pacing, based on whether RV lead 18 and/or LV lead 20 detects an intrinsic ventricular depolarization within a defined time interval following the atrial sensed or paced event.

IMD 16 also provides defibrillation therapy and/or cardioversion therapy via electrodes located on at least one of the leads 18, 20, 22. For example, IMD 16 detects arrhythmia of heart 12, such as fibrillation of ventricles 28 and 32, and delivers defibrillation therapy to heart 12 in the form of electrical pulses. In some examples, IMD 16 is programmed to deliver a progression of therapies, e.g., pulses with increasing energy levels, until a fibrillation of heart 12 is stopped. IMD 16 may detect fibrillation employing one or more known fibrillation detection techniques. In other examples, IMD 16 delivers anti-tachycardia pacing (ATP) or cardioversion in response to detecting tachycardia of ventricles 28 and 32.

In examples described herein, IMD 16 detects an atrial tachyarrhythmia, such as atrial fibrillation, and delivers electrical stimulation to right atrium 26 and left atrium 36 symmetrically to terminate the tachyarrhythmia. In particular, IMD 16 controls a plurality of electrodes arranged symmetrically on the atrial septum of heart 12 between right atrium 26 and left atrium 36 to deliver overdrive pacing followed abruptly by a first underdrive pacing at a first frequency and a second underdrive pacing at a second frequency to right atrium 26 and left atrium 36. The electrodes on the atrial septum are configured to produce strong and uniform depolarization waves that propagate symmetrically in both right atrium 26 and left atrium 36 of heart 12. Delivering overdrive and underdrive pacing in sequence with an abrupt transition there between may act to inhibit continuation of any fibrillating waves that present during the overdrive pacing phase.

Although the examples disclosed with reference to FIGS. 1-8 are generally described in the context of detection and termination of atrial tachyarrhythmias, and, in particular to atrial fibrillation, the same techniques may be applied to other tachyarrhythmias including, e.g., ventricular tachyarrhythmias, such as ventricular fibrillation. For example, IMD 16 may detect a ventricular tachyarrhythmia, such as ventricular fibrillation, and deliver electrical stimulation to right ventricle 28 and left ventricle 32 to terminate the tachyarrhythmia. In particular, IMD 16 may control a plurality of electrodes arranged symmetrically on the ventricular septum of heart 12 between right ventricle 28 and left ventricle 32 to deliver overdrive pacing followed abruptly by a first underdrive pacing at a first frequency and a second underdrive pacing at a second frequency to right ventricle 28 and left ventricle 32. Delivering overdrive and the first underdrive pacing in sequence with an abrupt transition there between may act to inhibit continuation of any fibrillating waves that present during the overdrive pacing phase. For simplicity, however, the disclosed examples are generally described in the context of techniques for treating atrial tachyarrhythmias.

In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device or other peripheral device.

A user, such as a physician, technician, surgeon, electrophysiologist, or other clinician, interacts with programmer 24 to communicate with IMD 16. For example, the user interacts with programmer 24 to retrieve physiological or diagnostic information from IMD 16. A user may also interact with programmer 24 to program IMD 16, e.g., select values for operational parameters of the device.

In one example, the user employs programmer 24 to retrieve information from IMD 16 regarding the rhythm of heart 12, trends therein over time, or arrhythmic episodes. As another example, the user employs programmer 24 to retrieve information from IMD 16 regarding other sensed physiological parameters of patient 14 or information regarding the therapy delivered to patient 14, such as the duration of overdrive pacing applied in response to a sensed atrial tachyarrhythmia episode. As another example, the user employs programmer 24 to retrieve information from IMD 16 regarding the performance or integrity of IMD 16 or other components of system 10, such as leads 18, 20 and 22, or a power source of IMD 16. In another example, the user interacts with programmer 24 to program, e.g., select parameters for, therapies provided by IMD 16, such as pacing, cardioversion, and/or defibrillation.

IMD 16 and programmer 24 may communicate via various wireless communication techniques. Examples of communication techniques include low frequency or radiofrequency (RF) telemetry, but other techniques are also contemplated. In some examples, programmer 24 includes a programming head that may be placed proximate to the patient's body near the IMD 16 implant site in order to improve the quality or security of communication between IMD 16 and programmer 24.

Figure 2:
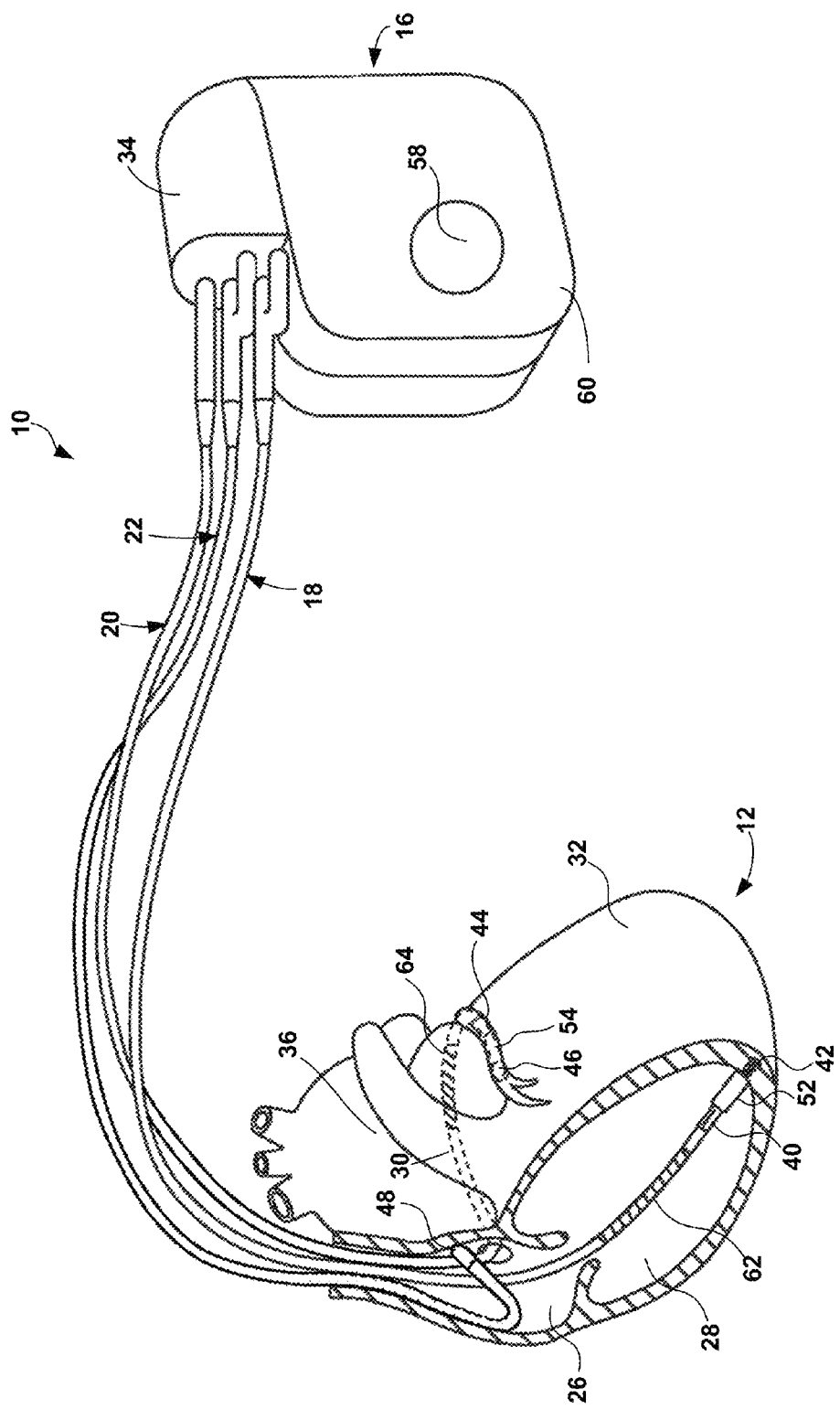
FIG. 2 is a conceptual diagram further illustrating the IMD and leads of the system of FIG. 1 in conjunction with the heart.

FIG. 2 is a conceptual diagram illustrating IMD 16 and leads 18, 20, 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths or cable conductors running through different, mutually isolated lumina in the lead body. One or more electrodes are located toward the distal ends of each of leads 18, 20, 22. For example, bipolar electrodes 40 and 42 are located adjacent to a distal end of lead 18 in right ventricle 28. In addition, bipolar electrodes 44 and 46 are located adjacent to a distal end of lead 20 in left ventricle 32.

As will be described below, RA lead 22 includes a plurality of electrodes connected to the lead toward a distal end thereof and configured to be arranged symmetrically on the atrial septum of heart 12 between right atrium 26 and left atrium 36. Arranging the electrodes symmetrically on the atrial septum as disclosed herein enables pacing pulses delivered via the electrodes to produce strong and uniform depolarization waves that propagate symmetrically in both right atrium 26 and left atrium 36 of heart 12 and with which the pacing techniques described herein may be employed to terminate atrial tachyarrhythmia episodes. The set of electrodes arranged toward the distal end of RA lead 22 is represented schematically in FIG. 2 as element 48. The electrode configuration of lead 22 is described in greater detail with reference to FIG. 3 below.

With respect to leads 18 and 20, electrodes 40 and 44 may take the form of ring electrodes, while electrodes 42 and 46 may take the form of extendable helix tip electrodes mounted retractably within insulative electrode heads 52 and 54 respectively. In some examples, one or both of electrodes 42 and 46 take the form of pre-exposed helix tip electrodes. In other examples, electrodes 42 and 46 take the form of small circular electrodes at the tip of a tined lead or other fixation element. Leads 18 and 20 also include elongated electrodes 62 and 64 respectively, which may take the form of a coil. Each of the electrodes 40, 42, 44, 46, 48, 62, and 64 are electrically coupled to, e.g., a respective one of the coiled conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define additional housing electrodes. In some examples, housing electrode 58 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 58, 62, and 64. The electrical signals are conducted to IMD 16 from the electrodes via the respective leads 18, 20, 22 or, in the case of housing electrode 58, a conductor coupled to housing electrode 58. IMD 16 may sense such electrical signals via any bipolar combination of electrodes 40, 42, 44, 46, 58, 62, 64, and the set of electrodes 48 connected to RA lead 22. Furthermore, any of the electrodes 40, 42, 44, 46, 58, 62, 64, and any of the set of electrodes 48 may be used for unipolar sensing in combination with housing electrode 58.

In some examples, IMD 16 delivers pacing pulses via bipolar combinations of electrodes 40, 42, 44, and 46, and the set of electrodes 48 to produce depolarization of cardiac tissue of heart 12. In other examples, IMD 16 delivers pacing pulses via any of electrodes 40, 42, 44, 46, and 48 in combination with housing electrode 58 in a unipolar configuration. For example, electrodes 40, 42, and/or 58 may be used to deliver RV pacing to heart 12. Additionally or alternatively, electrodes 44, 46, and/or 58 are used to deliver LV pacing to heart 12, and one or more of the set of electrodes 48 and/or 58 are used to deliver RA pacing to heart 12. As described previously, RV pacing, e.g., via electrodes 40, 42, and/or 58, may be used in combination with LV pacing, e.g., via electrodes 44, 46, and/or 58, to synchronize contraction of both ventricles. This type of biventricular pacing is commonly referred to as cardiac resynchronization therapy (CRT). In another example, electrodes 48 are arranged symmetrically on the atrial septum of heart 12 are used to produce depolarization waves that propagate symmetrically in both right atrium 26 and left atrium 36 of heart 12 and with which the pacing techniques described herein may be employed to terminate atrial tachyarrhythmia episodes.

Furthermore, IMD 16 may deliver defibrillation pulses to heart 12 via any combination of elongated electrodes 62 and 64 and housing electrode 58. In some examples, electrodes 58, 62, 64 are used to deliver cardioversion pulses to heart 12. Electrodes 62 and 64 may be fabricated from any suitable electrically conductive material, such as, but not limited to, platinum, platinum alloy or other materials known to be usable in implantable defibrillation electrodes.

Figure 3:
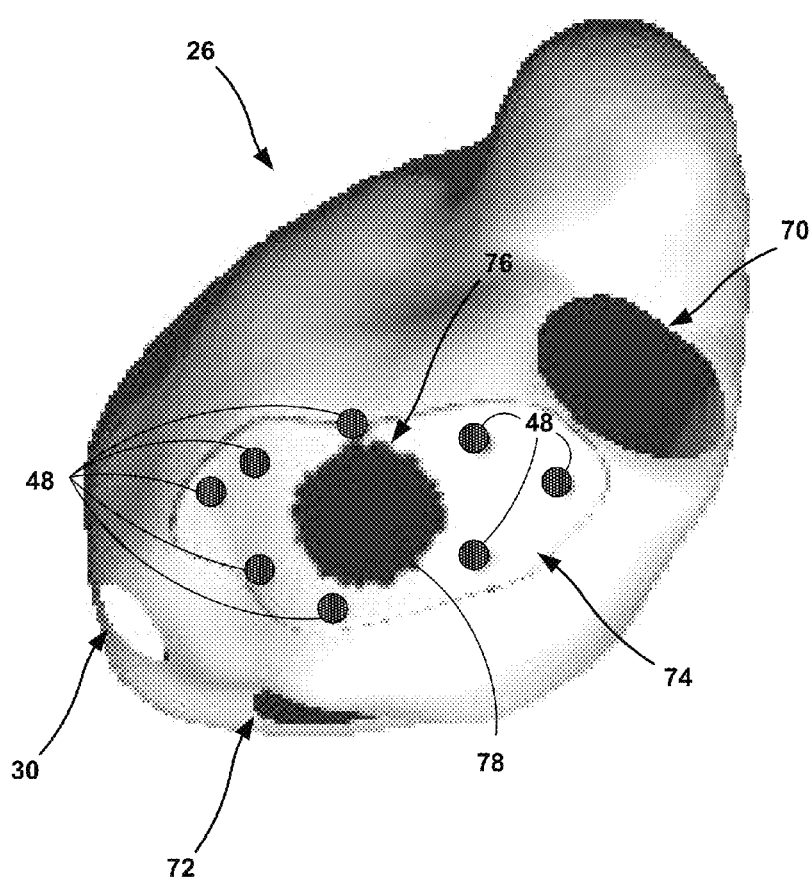
FIG. 3 is a conceptual diagram illustrating an example implantation location for electrodes of a right atrial lead on the atrial septum of a heart.

FIG. 3 is a conceptual diagram illustrating an example implantation location for electrodes 48 connected to RA lead 22. For clarity, RA lead 22 is not shown in FIG. 3. FIG. 3 illustrates the surface of right atrium 26 separated from the other chambers of heart 12. Illustrated in conjunction with right atrium 26 are the superior vena cava 70, inferior vena cava 72, coronary sinus 30, atrial septum 74, and fossa ovalis 76. Fossa ovalis 76 is an embryonic remnant of the foramen ovale, which is a hole in atrial septum 74 that normally closes shortly after birth. The periphery of fossa ovalis 76 is referred to herein as septum ring 78. Although not illustrated in FIG. 3, the distal portion of RA lead 22 will generally be advanced to its implantation location within right atrium 26 intravenously and through superior vena cava 70 (or, in some cases, inferior vena cava 72). Lead 22 may be secured to atrial septum 74 by any number of actively or passively deployed fixation members including, e.g., barbs, tines, hooks, helical fixation members, adhesives, balloons, or the like. In the illustrated example, a number of sense/stimulation electrodes 48 are arranged on atrial septum 76 that separates right atrium 26 and left atrium 36. Electrodes 48 are arranged generally symmetrically about fossa ovalis 76. In the example of FIG. 3, electrodes 48 are arranged in a ring around the periphery of fossa ovalis 76, i.e. around septum ring 78. Arranging electrodes 48 on atrial septum 74 of heart 12 in the manner illustrated in FIG. 3 enables IMD 16 to produce strong and uniform depolarization waves that propagate symmetrically in both right atrium 26 and left atrium 36 of heart 12 and that may act to terminate atrial fibrillation episodes. Electrodes 48 may include ring, helical, paddle, or any other electrode or combination capable of symmetrical arrangement on atrial septum 74 of heart 12.

Although FIG. 3 shows electrodes 48 arranged generally in a ring around septum ring 78, other arrangements are also included in examples disclosed herein. In some examples, electrodes 48 include an array with an equal number of electrodes arranged on either side of some reference on atrial septum 74. For example, an array of electrodes may be arranged symmetrically on atrial septum 74 about fossa ovalis 76, with an equal number of electrodes located generally on opposing sides of the reference location. In another example, electrodes 48 are arranged generally in a ring as shown in FIG. 3, but the ring is located with respect to some other reference point on atrial septum 74 including, e.g., coronary sinus ostium from which coronary sinus 30 extends toward a region adjacent to the free wall of left ventricle 32 of heart 12 (see FIGS. 1 and 2).

As noted above, although the examples disclosed herein with reference to FIGS. 1-8 are generally described in the context of atrial tachyarrhythmias, the same techniques may be applied to other tachyarrhythmias including, e.g., ventricular tachyarrhythmias, such as ventricular fibrillation. With reference to FIG. 3 and, more generally, the arrangement of electrodes 48 on the septum of heart 12, electrodes 48 may alternatively be arranged symmetrically on the ventricular septum (not shown) of the patient's heart to treat ventricular tachyarrhythmias, such as ventricular fibrillation.

In addition to arranging electrodes 48 on the septum of heart 12, e.g. as shown in FIG. 3 arranged on atrial septum 74 of the heart, electrodes 48 may also be arranged epicardially in a transition zone between right atrium 26 and left atrium 36. Additionally, in examples directed to treating ventricular arrhythmias, electrodes 48 may be arranged epicardially in a transition zone between right ventricle 28 and left ventricle 32. In this manner, electrodes 48 may be arranged outside of heart 12 in positions that correspond, relative to the atria or ventricles, to the septum, which is only accessible through the chambers of the heart, e.g. through right atrium 26. Arranging electrodes 48 epicardially provides an alternative placement location that may require less invasive surgical procedures.

Referring again to FIG. 3, the distal portion of lead 22 may include any of a variety of features to facilitate positioning of electrodes 48 as described with reference to FIG. 3. For example, the distal portion of lead may be furcated or branched, with each branch including one or more electrodes 48. As another example, the distal portion of lead 22 may expand or be expanded into a structure, e.g., spherical, conical, trapezoidal, or rectangular, which includes electrodes 48 on a distal portion of the structure. In some examples, the distal portion of lead 22 may include electrodes arranged along an axis, and also include nitinol or the like, such that during implantation, e.g., after removal of a stylet, the distal portion may assume a curved or other shape that positions electrodes 48 as describe with reference to FIG. 3.

Figure 4:
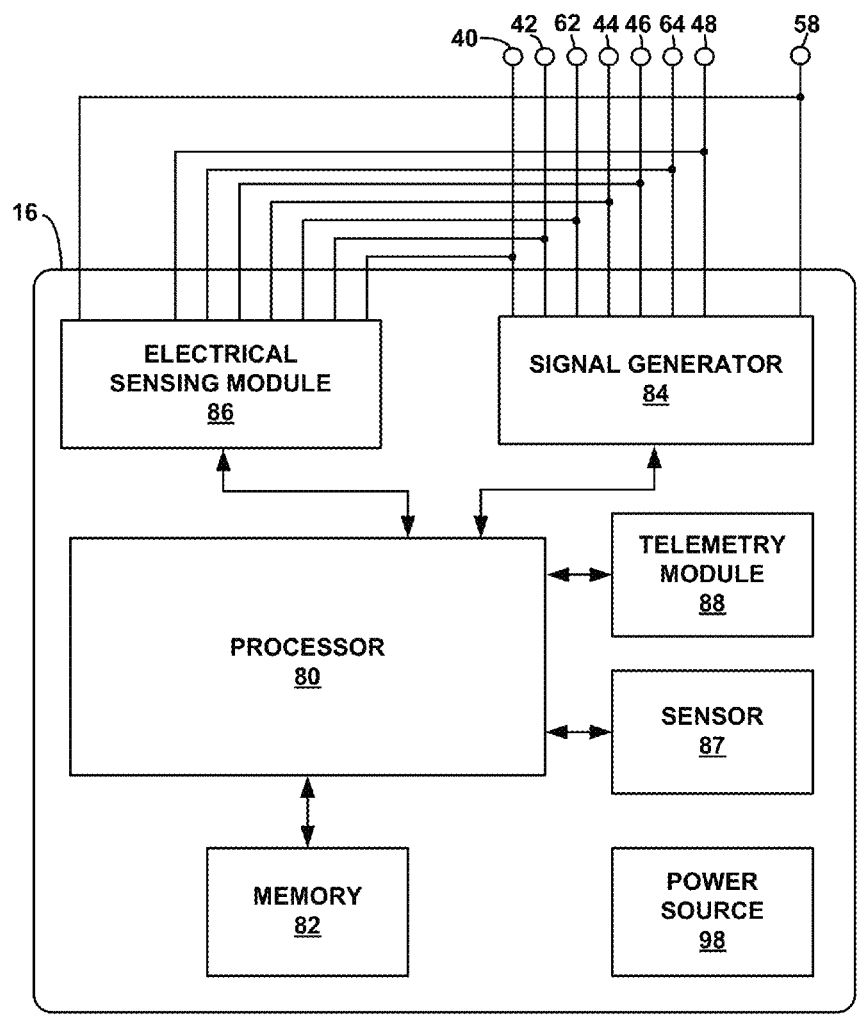
FIG. 4 is a block diagram illustrating constituent components of the IMD of FIG. 1 according to one example configuration.

FIG. 4 is a functional block diagram illustrating one example configuration of IMD 16. In the example illustrated by FIG. 4, IMD 16 includes a processor 80, memory 82, signal generator 84, electrical sensing module 86, sensor 87, telemetry module 88, and power source 98. Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include a microprocessor, a controller, a digital signal processor (DSP), an application specific integrated circuit (ASIC), a field-programmable gate array (FPGA), or equivalent discrete or integrated logic circuitry. In some examples, processor 80 includes multiple components including any combination of microprocessors, controllers, DSPs, ASICs, and FPGAs, as well as other discrete or integrated logic circuitry. The functions attributed to processor 80 herein may be embodied as software, firmware, hardware or any combination thereof. Processor 80 controls signal generator 84 to deliver stimulation therapy to heart 12 according to operational parameters or programs, which may be stored in memory 82.

Signal generator 84 is electrically coupled to electrodes 40, 42, 44, 46, 48, 58, 62, and 64, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks to heart 12 via at least two of electrodes 58, 62, 64. Signal generator 84 may deliver pacing pulses via electrodes 40, 44, 48 coupled to leads 18, 20, and 22, respectively, and/or helical electrodes 42 and 46 of leads 18 and 20 respectively. Signal generator 84 may also deliver pacing to terminate atrial tachyarrhythmia, e.g., atrial fibrillation, via electrodes 48 of RA lead 22, e.g., in a bipolar configuration or in a unipolar configuration in combination with housing electrode 58. In some examples, signal generator 84 delivers stimulation in the form of electrical pulses. In other examples, signal generator 84 delivers stimulation in the form of other signals, such as sine waves, square waves, or other substantially continuous time signals.

In some examples, signal generator 84 is configured to deliver pacing to heart 12 to terminate an atrial tachyarrhythmia episode. For example, processor 80 may control signal generator 84 to deliver pacing pulses to heart 12 via, e.g., the set of electrodes 48 connected to RA lead 22 and arranged on atrial septum 74, at an overdrive pacing frequency followed abruptly by delivering pulses at a first underdrive pacing frequency and a second underdrive pacing frequency. This stimulation pattern and location may act to effectively terminate the atrial tachyarrhythmia by reducing the likelihood that tachyarrhythmia waves in a portion of the atria may regain control of the atrial rhythm. More particularly, the overdrive pacing may disrupt the tachyarrhythmia waves in a region of atrial tissue that includes tissue of both atria around the septum, providing an opportunity for the first and the second underdrive pacing phases to be installed, and thereafter capture both atria and terminate the tachyarrhythmia.

Memory 82 may store values for stimulation parameters that processor 80 accesses to control delivery of stimulation by signal generator 84. Such stimulation parameters include pulse duration, pulse train duration, pulse amplitude, pulse frequency, and pulse train frequency or duty cycle. In some examples, memory 82 stores the respective durations of time that signal generator 84 delivers overdrive and the first and the second underdrive pacing. The periods of time that signal generator 84 delivers overdrive pacing and the first and the second underdrive pacing may be important to the effectiveness of the pacing in terminating an atrial tachyarrhythmia episode. In some examples, memory 82 stores fixed durations for both the overdrive and underdrive phases of the pacing therapy delivered by signal generator 84. In one example, processor 80 controls signal generator 84 to deliver overdrive pacing for a time period in a range from approximately 10 seconds to approximately 30 seconds. Additionally, in one example, processor 80 controls signal generator 84 to deliver a single pacing pulse of the first underdrive pacing at the first frequency and delivers the second underdrive pacing at the second frequency for approximately 1.5 seconds. In another example, processor 80 controls signal generator 84 to deliver in a range from 1 to 5 pacing pulses of the first underdrive pacing at the first frequency. In another example, processor 80 controls signal generator 84 to deliver in a range from 1 to 3 pacing pulses of the first underdrive pacing at the first frequency. In such examples, the particular fixed overdrive and underdrive pacing time periods may be stored in memory 82 for access by processor 80.

In other examples, memory 82 stores a fixed duration for only the first and the second underdrive phases, while the duration of overdrive pacing delivered by signal generator 84 is based on depolarization/repolarization patterns of heart 12 sensed by electrical sensing module 86 during delivery of the overdrive pacing. For example, overdrive pacing may be delivered until the depolarization waves sensed in right atrium 26 and left atrium 36 have been sufficiently captured by the overdrive pacing therapy, as substantiated by the level of entrainment (the cycle length being in most atrial locations the same as the septal overdrive pacing cycle length). Upon initial delivery of overdrive pacing to right atrium 26 and left atrium 36 of heart 12 via electrodes 48 on atrial septum 74 by signal generator 84, remnants of the atrial fibrillation depolarization wave patterns may persist in different parts of heart 12. In order to effectively terminate an atrial fibrillation episode, however, it may be necessary to continue overdrive pacing until a sufficient level of capture of the depolarization pattern of right atrium 26 and left atrium 36 has occurred. Therefore, signal generator 84 may be controlled by processor 80 to deliver overdrive pacing until it is clear based on an analysis of the depolarization waves sensed in right atrium 26 and left atrium 36 by sensing module 86 that the atrial tissue has been sufficiently captured, and only then will the signal generator abruptly transition to delivering the first underdrive pacing via electrodes 48 on atrial septum 74.

In addition to storing time durations for delivering overdrive and underdrive pacing, memory 82 may store pacing protocol parameters for delivering stimulation during both of these phases of therapy. In some examples, the frequency of pacing delivered to heart 12 by signal generator 84 is a function of the cycle length of the atrial tachyarrhythmia episode ("AFCL" in the case of atrial fibrillation). In other words, the frequency of pacing during both the overdrive pacing phase and the first and the second underdrive pacing phases may be based on the frequency of atrial tachyarrhythmia sensed by sensing module 86. In one example, overdrive pacing is delivered at a frequency in a range from approximately 62% to approximately 74% of AFCL, the first underdrive pacing is delivered at a first frequency of 130% of AFCL, and the second underdrive pacing is delivered at a second frequency of approximately 180% AFCL. In another example, overdrive pacing is delivered at a frequency of approximately 64% of AFCL, the first underdrive pacing is delivered at a first frequency of 130% of AFCL, and the second underdrive pacing is delivered at a second frequency of approximately 180% AFCL. In any case, signal generator 84 may deliver stimulation with a fixed pulse frequency, or in an incremental interval pattern by which stimulation frequency is ramped down from the beginning to end of the stimulation phase. For example, stimulation during the overdrive pacing may be delivered at 64% AFCL throughout the entire phase, or the pacing may be ramped down from 62% AFCL to 74% AFCL before processor 80 controls signal generator 84 to abruptly transition to the underdrive pacing phase.

In some examples, stimulation delivered by signal generator 84 as controlled by processor 80 may be defined by predetermined or fixed parameter values as specified in one or more therapy programs stored in memory 82. In other examples, however, stimulation is delivered by a closed loop system in which one or more stimulation parameter values are varied over time based on one or more feedback loops. For example, processor 80 may control signal generator 84 to begin delivering stimulation according to a baseline set of stimulation parameter values, e.g. pacing amplitude, frequency, and duration. Thereafter, processor 80 may control signal generator 84 to vary the values of one or more of the baseline set of parameters as function of the effectiveness of the therapy delivered. For example, processor 80 may control signal generator 84 to vary the pacing frequency and/or the duration of the overdrive and/or the first and/or the second underdrive pacing phases, as well as any time delay between the two phases based on, e.g., how well previous stimulation captured depolarization in right atrium 26 and left atrium 36 or how effective the stimulation was in terminating or attenuating atrial tachyarrhythmia waves propagating through heart 12.

Signal generator 84 may include a switch module and processor 80 may use the switch module to select, e.g., via a data/address bus, which of the available electrodes are used to deliver stimulation signals including, e.g., defibrillation, and/or pacing stimulation signals. The switch module may include a switch array, switch matrix, multiplexer, or any other type of switching device suitable to selectively couple a signal to selected electrodes.

Electrical sensing module 86 monitors signals from at least one of electrodes 40, 42, 44, 46, 48, 58, 62, or 64 in order to monitor electrical activity of heart 12. Electrical sensing module 86 may also include a switch module to select which of the available electrodes are used to sense the heart activity. In some examples, processor 80 selects the electrodes that function as sense electrodes, or the sensing configuration, via the switch module within electrical sensing module 86, e.g., by providing signals via a data/address bus.

In some examples, electrical sensing module 86 includes multiple detection channels, each of which comprise an amplifier. Each sensing channel detects electrical activity in respective chamber of heart 12, and may be configured to detect either R-waves or P-waves. In some examples, electrical sensing module 86 or processor 80 includes an analog-to-digital converter for digitizing the signal received from a sensing channel for electrogram signal processing by processor 80. In response to the signals from processor 80, the switch module within electrical sensing module 86 couples the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of electrodes 40, 42, 44, 46, 48, 58, 62, or 64 appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by stimulation generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect a tachyarrhythmia event, such as an atrial or ventricular fibrillation or tachycardia and/or detect a heart rate, such as an atrial rate or ventricular rate.

In one example, processor 80 uses the count in the interval counters provided by sensing module 86 to sense an atrial fibrillation or other atrial tachyarrhythmia episode in heart 12. Processor 80 then controls signal generator 84 to deliver stimulation via electrodes 48 arranged on atrial septum 74 to right atrium 26 and left atrium 36. In particular, processor 80 controls signal generator 84 to deliver overdrive pacing followed abruptly by a first underdrive pacing at a first frequency and a second underdrive pacing at a second frequency to terminate the atrial fibrillation episode. During delivery of overdrive pacing, sensing module 86 continues to monitor electrical activity of heart 12 to detect, e.g., when the depolarization waves in right atrium 26 and left atrium 36 have been sufficiently captured by the overdrive pacing pattern being applied by signal generator 84. For example, signal generator 84 may be controlled by processor 80 to deliver overdrive pacing until an analysis of the depolarization waves sensed in right atrium 26 and left atrium 36 by sensing module 86 indicate that a sufficient portion of the atrial tissue has been captured. After sensing module 86 detects sufficient local capture of right atrium 26 and left atrium 36, processor 80 controls signal generator 84 to abruptly transition from overdrive pacing to the first underdrive pacing for one or more pacing pulses and then to continue by delivering the second underdrive pacing for a fixed duration of time including, e.g., a duration of time stored in memory 82, upon completion of the first underdrive pacing.

Processor 80 may also derive other physiological parameters from signals sensed via electrical sensing module 86. For example, processor 80 may establish one or more indicators of ejection fraction and/or heart failure status from electrical signals sensed via electrical sensing module 86. In particular, impedance signals may be used to determine flow or pressure, which may indicate ejection fraction and/or heart failure status.

IMD 16 also includes one or more sensors 87 separate from electrodes 40, 42, 44, 46, 48, 58, 64 and 66. Via a signal generated by sensor 87, processor monitors one or more physiological parameters indicative of cardiac contraction, autonomic tone, heart failure, and/or ejection fraction. Examples of sensors 87 that generate a signal indicative of cardiac contraction include a intracardiac or intravascular pressure sensor, an accelerometer or other sensor capable of detecting heart or blood sounds, vibrations, or motion, an optical or ultrasonic sensor capable or detecting changes in flow associated with cardiac contractions, or an optical sensor capable of detecting oxygen saturation changes associated with cardiac contractions. In some examples, processor 80 detects cardiac contractions based on signals from one or more sensors 87, and detects arrhythmias based on the detected cardiac contractions.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

In some examples, processor 80 transmits indications of detected atrial tachyarrhythmias and the duration and frequency of overdrive pacing and the first and the second underdrive pacing to be delivered subsequent to the detected tachyarrhythmias via telemetry module 88. Processor 80 may also transmit, via telemetry module 88, information regarding a response to the atrial tachyarrhythmia termination pacing, e.g., detected by electrical sensing module 86.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis. In other examples, power source 90 may include a supercapacitor.

Figure 5:
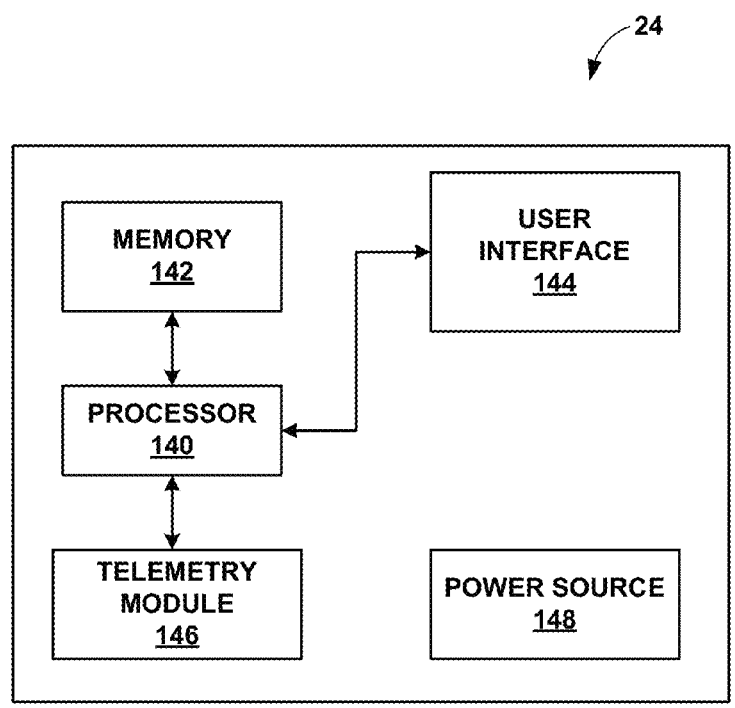
FIG. 5 is a block diagram of illustrating constituent components of the external programmer of the system of FIG. 1 according to one example configuration.

FIG. 5 is a block diagram of an example configuration of programmer 24. As shown in FIG. 5, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of operational parameters), generate new therapy programs, or modify therapy programs for IMD 16. The clinician may interact with programmer 24 via user interface 144 which may include a display to present a graphical user interface to a user, and a keypad or another mechanism for receiving input from a user.

In some examples, a user employs programmer 24 to program one or more parameters by which IMD 16 delivers pacing to heart 12 to terminate a tachyarrhythmia episode including, e.g. an atrial fibrillation episode. For example, a user may employ programmer 24 to program parameters including pulse duration, pulse train duration, pulse amplitude, pulse frequency, and pulse train frequency or duty cycle into memory 82 for access by processor 80 to control delivery of pacing by signal generator 84 to heart 12. In some examples, a user employs programmer 24 to program fixed durations of time that signal generator 84 delivers one or more of overdrive and the first and the second underdrive pacing phases. However, in other examples, a user employs programmer 24 to program a fixed duration for only the first and the second underdrive phases, while the duration of overdrive pacing delivered by signal generator 84 is based on depolarization/repolarization patterns of heart 12 sensed by electrical sensing module 86 during delivery of the overdrive pacing. The values of these and other parameters may be, e.g., programmed globally across a number of therapy programs, or different values for one or more of the parameters may be programmed into a number of different programs.

Processor 14 can take the form one or more microprocessors, DSPs, ASICs, FPGAs, programmable logic circuitry, or the like, and the functions attributed to processor 102 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 4).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 is configured to provide some or all of the functionality ascribed to processor 80 of IMD 16 herein. For example, processor 140 may receive indications of cardiac depolarizations or contractions, a signal from sensing module 86 or sensors 87, and/or information regarding detected atrial tachyarrhythmias from IMD 16 via telemetry module 146. In some examples, processor 140 initiates or modifies atrial tachyarrhythmia termination pacing, as described herein with reference to processor 80 of IMD 16. Additionally, parameters defining pacing delivered to heart 12 by IMD 16 may be programmed by programmer 24 to be stored in memory 142 of programmer 24 in addition to or in lieu of storing pacing parameters in memory 82 of IMD 16.

Figure 6:
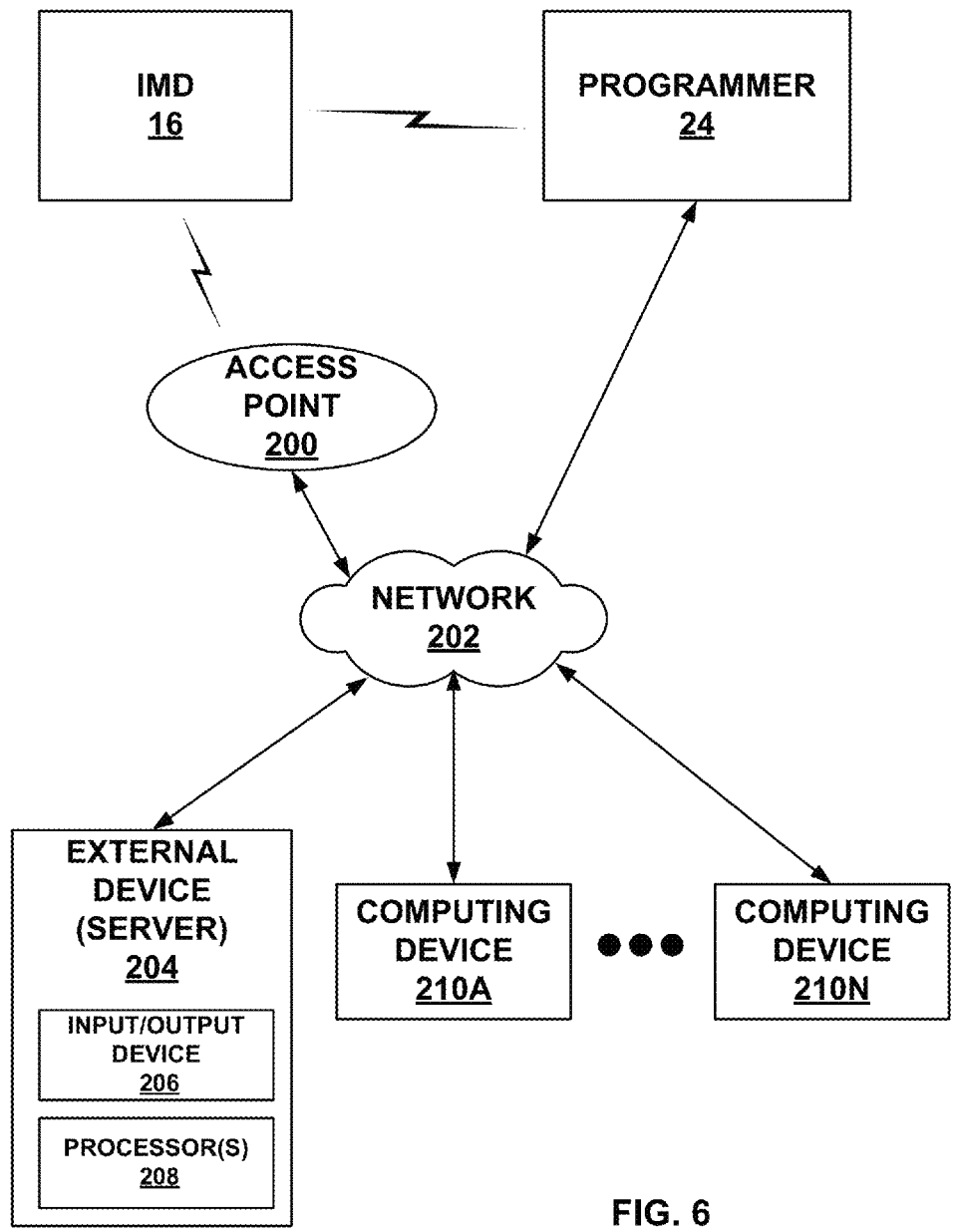
FIG. 6 is a block diagram illustrating an example system that includes an external device, such as a server, and computing devices that are coupled to the IMD and programmer shown in FIG. 1 via a network.

FIG. 6 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 is coupled to network 202 through different forms of connections, including wired or wireless connections. In some examples, access point 200 is co-located with patient 14 and includes one or more programming units and/or computing devices (e.g., one or more monitoring units) that perform various functions and operations described herein. For example, access point 200 may include a home-monitoring unit that is co-located with patient 14 and that may monitor the activity of IMD 16.

In some cases, server 204 is configured to provide a secure storage site for data that has been collected from IMD 16 and/or programmer 24. Network 202 may comprise a local area network, wide area network, or global network, such as the Internet. In some cases, programmer 24 or server 206 assembles data in web pages or other documents for viewing by trained professionals, such as clinicians, via viewing terminals associated with computing devices 210A-210N. The illustrated system of FIG. 6 may be implemented, in some aspects, with general network technology and functionality similar to that provided by the Medtronic CareLink® Network developed by Medtronic, Inc., of Minneapolis, Minn.

In some examples, processor 208 of server 204 is configured to provide some or all of the functionality ascribed to processor 80 of IMD 16 herein. For example, processor 208 may receive indications of cardiac depolarizations or contractions, a signal from sensing module 86 or sensors 87, and/or information regarding detected atrial arrhythmias from IMD 16 via access point 200 or programmer 24 and network 202. Processor 208 may also initiate or modify atrial tachyarrhythmia termination pacing, as described herein with reference to processor 80 of IMD 16. In some examples, server 204 relays information received from one or more of IMD 16 or programmer 24 to one or more of computing devices 210 via network 202. A processor of a computing device 210 may also provide some or all of the functionality ascribed to processor 80 of IMD 16 herein.

Figure 7:
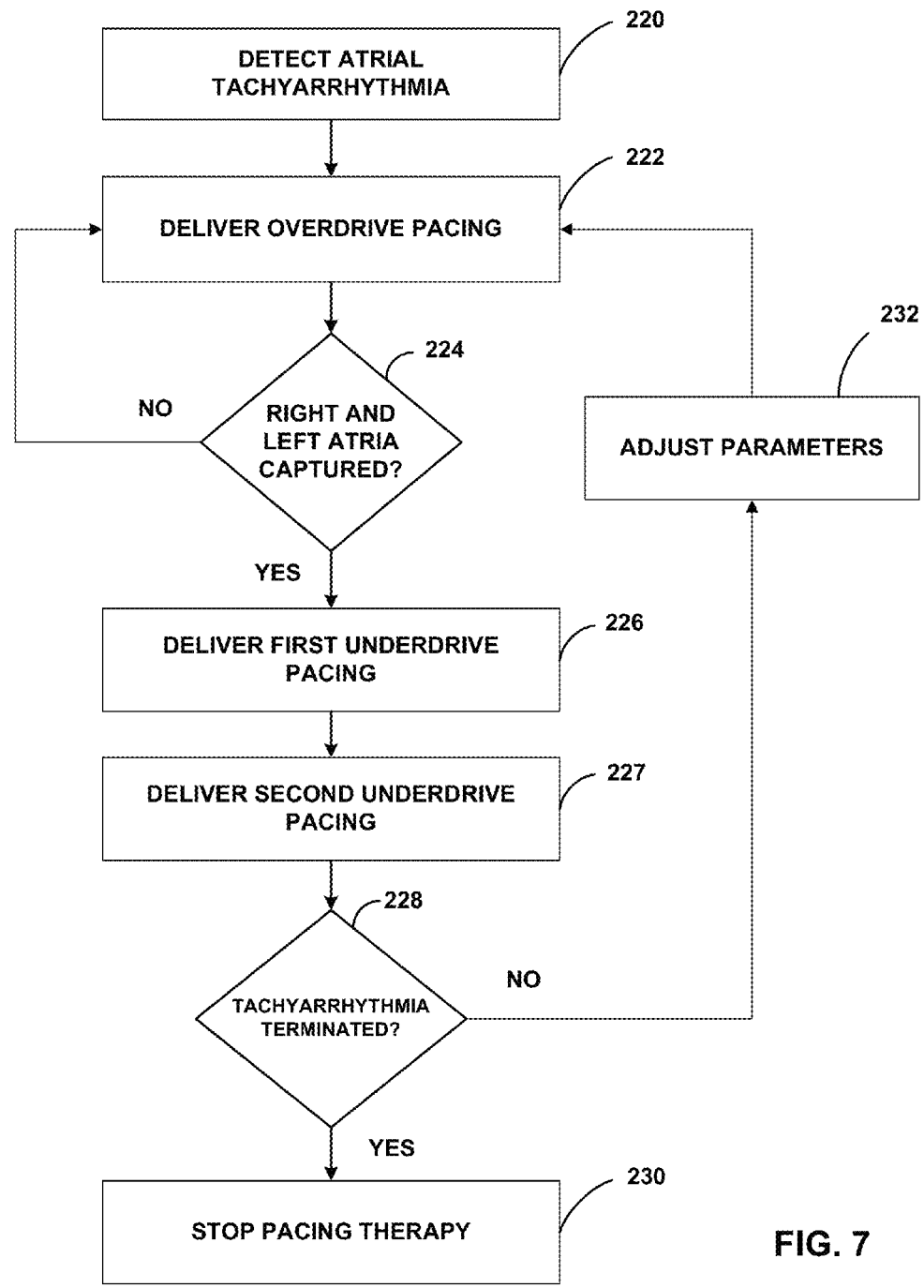
FIG. 7 is a flowchart illustrating an example method of terminating a detected atrial tachyarrhythmia episode by delivery of overdrive pacing followed abruptly by underdrive pacing.

FIG. 7 is a flowchart illustrating a method of employing pacing techniques to terminate a detected atrial tachyarrhythmia episode. The example method of FIG. 7 generally includes detecting an atrial tachyarrhythmia, e.g., fibrillation, episode (220), delivering overdrive pacing via electrodes arranged symmetrically on atrial septum 74 of heart 12 (222), and determining whether tissue of the right atrium 26 and left atrium 36 proximate to the septum has been sufficiently captured by the applied overdrive pacing (224). If right atrium 26 and left atrium 36 have not been sufficiently captured, overdrive pacing is continued (222). If, however, right atrium 26 and left atrium 36 have been sufficiently captured, there is an abrupt transition to delivering a first underdrive pacing at a first frequency (226) and then delivering a second underdrive pacing at a second frequency (227). The method of FIG. 7 also includes determining whether the detected atrial fibrillation episode has terminated (228). If the episode has terminated, the atrial tachyarrhythmia termination pacing is stopped (230). If, however, the atrial fibrillation episode has not terminated, the parameters by which stimulation is delivered are adjusted (232) and overdrive pacing is applied again (222).

The method illustrated in FIG. 7 includes detecting an atrial tachyarrhythmia episode (220). In some examples, processor 80 of IMD 16 maintains an escape interval counter, e.g., a P-P interval counter, which is reset upon sensing of P-waves via one or more detection channels of electrical sensing module 86. The value of the count present in the escape interval counter when reset by sensed P-waves is used by processor 80 to measure the durations of P-P intervals. Processor 80 uses the count in the interval counter provided by sensing module 86 to detect an atrial tachyarrhythmia episode (220) in heart 12.

In some examples, IMD 16 continues to monitor heart 12 to determine if the detected atrial tachyarrhythmia is sustained before triggering any therapeutic response to the arrhythmia. For example, processor 80 may control sensing module 86 to continue monitoring the cardiac rhythm of heart 12 for a period of time stored in memory 82. A sustained atrial fibrillation episode includes, e.g., episodes lasting for more than approximately 30 seconds.

In the event an atrial tachyarrhythmia episode is detected, processor 80 then controls signal generator 84 to deliver stimulation to right atrium 26 and left atrium 36 of heart 12 via electrodes 48 arranged on atrial septum 74. In particular, processor 80 controls signal generator 84 to deliver overdrive pacing (222) via electrodes 48. Processor 80 may control signal generator 84 to deliver overdrive pacing with a pacing frequency that is less than a cycle length of the atrial tachyarrhythmia, and may be a function of the cycle length of the atrial tachyarrhythmia. In one example, in the case of atrial fibrillation, overdrive pacing is delivered at a frequency in a range from approximately 62% to approximately 74% of AFCL. In one example, processor 80 controls signal generator 84 to deliver overdrive pacing at a frequency of approximately 64% of AFCL. Signal generator 84 may deliver stimulation with a fixed pulse frequency, or in an incremental interval pattern by which stimulation frequency is ramped down from the beginning to end of the overdrive stimulation phase. For example, stimulation during the overdrive pacing phase may be delivered at 64% AFCL throughout the entire phase, or the pacing may be ramped down from 62% AFCL to 74% AFCL. Memory 82 may also store values for other stimulation parameters used during overdrive pacing including, e.g., pulse duration, pulse train duration, pulse amplitude, pulse frequency, and pulse train frequency.

In some examples, processor 80 controls signal generator 84 to deliver overdrive pacing to right atrium 26 and left atrium 36 for a fixed duration of time stored in memory 82, e.g., as part of a set of parameters organized in a therapy program. For example, processor 80 may control signal generator 84 to deliver overdrive pacing to right atrium 26 and left atrium 36 for a time period in a range from approximately 10 seconds to approximately 30 seconds. In other examples, however, sensing module 86 continues to monitor electrical activity of heart 12 during delivery of overdrive pacing to detect, e.g., when the tissue of right atrium 26 and left atrium 36 has been sufficiently captured (224) by the overdrive pacing pattern being applied by signal generator 84. Upon initial delivery of overdrive pacing to right atrium 26 and left atrium 36 of heart 12 via electrodes 48, remnants of the atrial tachyarrhythmia depolarization wave patterns may persist in different parts of the heart. In order to effectively terminate an atrial tachyarrhythmia episode, however, it may be necessary to continue overdrive pacing until a sufficient level of capture of the right atrium 26 and left atrium 36 has occurred. Therefore, signal generator 84 may be controlled by processor 80 to deliver overdrive pacing until the depolarization waves sensed in right atrium 26 and left atrium 36 by sensing module 86 indicate that the atrial tissue has been sufficiently captured (224). In one example, signal generator 84 may be controlled by processor 80 to deliver overdrive pacing until the depolarization waves sensed in right atrium 26 and left atrium 36 by sensing module 86 indicate that a sufficient portion of the atrial tissue has been captured. Regardless of whether overdrive pacing is delivered for a fixed duration of time or until sufficient local capture of right atrium 26 and left atrium 36 is sensed, processor 80 controls signal generator 84 to transition abruptly from delivering overdrive pacing to delivering a first underdrive pacing at a first frequency (226) to heart 12. As used herein, an abrupt transition means that there is no pacing frequency transition, e.g. ramping pacing frequency down, between the overdrive and the first underdrive pacing phases employed in the disclosed examples. Although IMD 16 transitions abruptly from overdrive to the first underdrive pacing, the device may nevertheless employ a transition time delay between pacing phases in some examples. For example, IMD 16 may employ a transition time delay of between and including approximately 0 and 300 milliseconds between delivering overdrive pacing and the first underdrive pacing.

In addition to delivering overdrive pacing (222) and the first underdrive pacing at the first frequency (226), processor 80 controls signal generator 84 to deliver a second underdrive pacing at a second frequency (227) to heart 12. Delivering overdrive pacing (222) followed abruptly by delivering the first underdrive pacing (226) and then delivering the second underdrive pacing (227) may act to effectively terminate the atrial tachyarrhythmia by reducing the likelihood that tachyarrhythmia waves in a portion of the atria may regain control of the atrial rhythm. More particularly, the overdrive pacing may disrupt the tachyarrhythmia waves in a region of atrial tissue that includes tissue of both atria around the septum, providing an opportunity for the first underdrive pacing to be installed, and thereafter capture the entirety of both atria with the second underdrive pacing and thereby terminate the tachyarrhythmia.

Processor 80 may control signal generator 84 to deliver the first underdrive pacing and/or the second underdrive pacing according to one or more protocols specifying pacing frequency as a function of the cycle length of the tachyarrhythmia, e.g., the AFCL. In one example, the first underdrive pacing is delivered at a first frequency of 130% AFCL and the second underdrive pacing is delivered at a second frequency of approximately 180% of AFCL. In one example, a single pacing pulse of the first underdrive pacing is delivered at the first frequency. In another example, multiple pacing pulses of the first underdrive pacing are delivered at the first frequency. In one example, the second underdrive pacing is delivered at the second frequency for approximately 1.5 seconds.

Signal generator 84 may deliver stimulation with a fixed pulse frequency, or in an incremental interval pattern by which stimulation frequency is ramped down from the beginning to end of the stimulation phase. For example, stimulation during the first underdrive pacing phase may be delivered at 130% AFCL throughout the entire phase, or the pacing may be ramped down from, e.g., 64% AFCL to 130% AFCL. Additionally, stimulation during the second underdrive pacing phase may be delivered at 180% AFCL throughout the entire phase, or the pacing may be ramped down from 130% AFCL to 180% AFCL. Memory 82 may also store values for other stimulation parameters of the underdrive pacing including, e.g., pulse duration, pulse amplitude, and pulse frequency.

Figure 8:
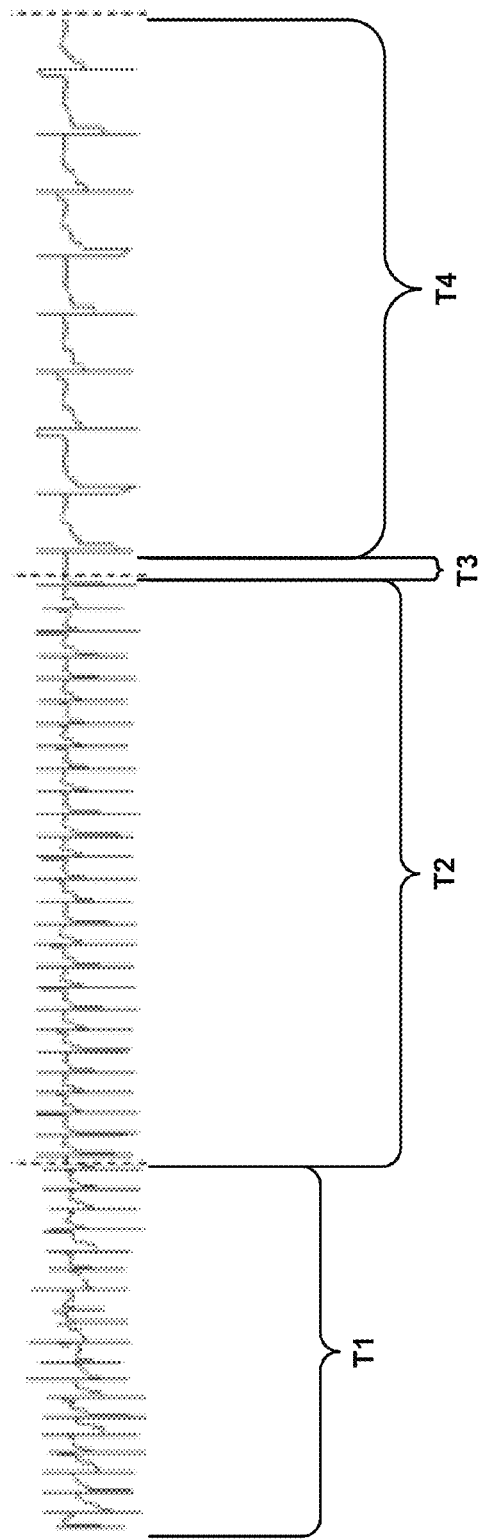
FIG. 8 illustrates an example atrial electrogram output during different phases of the method of FIG. 7.

FIG. 8 illustrates an example atrial electrogram output during different phases of the method of FIG. 7. In particular, FIG. 8 illustrates cardiac rhythm during a sustained period of atrial fibrillation, and a period of overdrive pacing followed abruptly by a period of first underdrive pacing at a first frequency and then a period of a second underdrive pacing at a second frequency. In FIG. 8, atrial fibrillation arrhythmia presents and persists for a period $T_1$. After the sustained period of atrial fibrillation, an IMD including, e.g., IMD 16 delivers overdrive pacing at a frequency of approximately 64% AFCL for a period of $T_2$. The overdrive pacing is followed abruptly by the delivery of the first underdrive pacing at a frequency of approximately 130% AFCL for a period $T_3$. Finally, in the example of FIG. 8, the second underdrive pacing is delivered at a second frequency of approximately 180% AFCL for a period $T_4$.

Referring again to FIG. 7, processor 80 may control sensing module 86 to monitor the cardiac rhythm of heart 12 to determine if the atrial fibrillation episode has been terminated (228) after the second underdrive pacing has been delivered (227), e.g., for a fixed duration of time stored in memory 82. In the event the episode has been terminated, processor 80 may control the signal generator 84 to stop the ATP therapy and resume a regular pacing therapy, such as RV, LV, or biventricular pacing program. In the event, however, the atrial fibrillation episode is not terminated, processor 80 may control sensing module 86 to initiate another cycle of delivering overdrive followed abruptly by the first underdrive pacing.

In some examples, stimulation delivered by signal generator 84 as controlled by processor 80 may be defined by fixed parameter values as specified in one or more therapy programs stored in memory 82. In such examples, when processor 80 initiates another cycle of the atrial tachyarrhythmia termination pacing to terminate the atrial tachyarrhythmia episode, the therapy may be delivered according to the same values for some or all of the parameters that defined therapy in the previous cycle, or processor 80 may cycle through parameters or programs on a set schedule. In other examples, however, stimulation is delivered by a closed loop system in which one or more stimulation parameter values are varied over time. Therefore, processor 80 may adjust one or more stimulation parameters (232) before initiating another cycle of atrial tachyarrhythmia termination pacing by delivering overdrive pacing (222) for a second time. For example, processor 80 may control signal generator 84 to begin delivering stimulation according to a baseline set of stimulation parameter values, e.g. pacing amplitude, frequency, and duration. Thereafter, processor 80 may control signal generator 84 to vary the values of one or more of the baseline set of parameters as function of the effectiveness of the therapy delivered. In one example, processor 80 controls signal generator 84 to vary the pacing frequency and the duration of the overdrive and the first and/or the second underdrive pacing phases, as well as any time delays between any two sequential phases based on, e.g., how well previous stimulation captured depolarization in right atrium 26 and left atrium 36 or how effective the stimulation was in attenuating atrial fibrillation waves propagating through heart 12.

A study was performed in which sustained AF was generated in a model based on human magnetic resonance images and membrane kinetics. Techniques in accordance with this disclosure, i.e. a combination of overdrive and underdrive pacing were applied to the model to determine AF termination rates for various pacing parameters. The procedures and results of the study are illustrated and described with reference to FIGS. 9-13.

Figure 9:
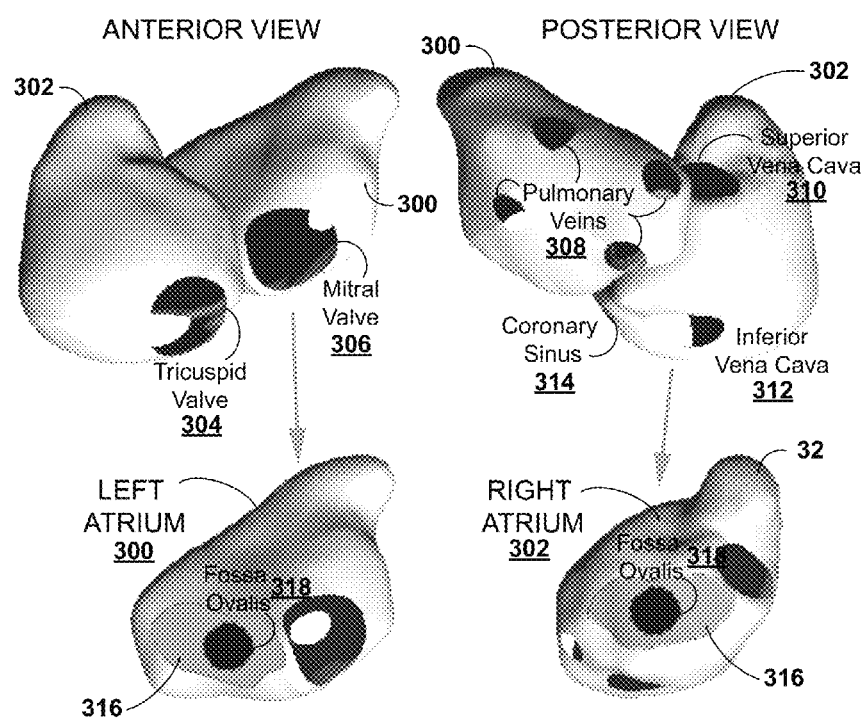
FIG. 9 is an image including anterior and posterior views of a three-dimensional monolayer atrial geometric model employed in a study of AF termination algorithms.

FIG. 9 is an image including anterior and posterior views of a three-dimensional monolayer atrial geometric model of left and right atria 300, 302, respectively, that was constructed for the study based on slice-by-slice segmentation of human magnetic resonance images. The resulting geometry included all major anatomical obstacles to propagation, including triscupid valve 304, mitral valve 306, pulmonary veins 308, superior vena cava 310, inferior vena cava 312, and coronary sinus 314. The geometric model illustrated in FIG. 9 includes the respective entries or exits of the foregoing vessels into and out of left and right atria 300, 302, instead of the actual vessels extending therefrom. The three-dimensional geometric model also included septal area 316 and fossa ovalis 318.

To allow the computation of atrial electrical activity propagation, the three-dimensional geometry was discretized using triangular elements, resulting in 50,000 nodes representing atrial cellular activity, with a 600 μm spatial resolution. Each node was connected to its neighbors via electrical resistors (with a set local resistivity) representing gap junctions. At each node, electrical cellular activity was modeled by a Luo-Rudy membrane kinetics model with ionic properties adapted to those of atrial membrane properties. The model was adjusted to mimic electrical remodeling as observed in permanent AF, such as shortening of action potential duration (APD). In particular, the K+ channel conductance was set to Gk equal to 0.423 milliseconds/cm$^2$, the Na+ channel conductance to GNa equal to 16 milliseconds/cm$^2$, and the L-type Ca2+ channel conductance to Gsi equal to 0.055 milliseconds/cm$^2$, resulting in an APD of 242 milliseconds during sinus rhythm. The resistivity value between two neighboring atrial cells was set to 200 Ωcm, resulting in a mean conduction velocity (CV) during sinus rhythm of 70 cm/s.

AF was initiated in the model by 20 Hz pacing for 3 seconds in the sinoatrial node region. When pacing was stopped, AF was sustained and was allowed to evolve freely during 10 minutes. The resulting AF dynamics showed multiple reentrant wavelets that continuously changed in size and direction, accompanied by important variations in AF cycle length (AFCL) over time. From the 10 minutes of simulated sustained AF, 40 instantaneous transmembrane potential maps (IC1 to IC40) were selected at 15 second intervals to form an AF database. These maps differed in terms of their activation patterns and were taken as AF initial conditions to test the effectiveness of the proposed septal pacing algorithm.

In the AF termination algorithm employed in the study, pacing was applied from septal area 316 of the model of FIG. 9. Septal pacing included simultaneous electrical stimulation of 1248 nodes located in the septal area (corresponding to a surface of 4.36 cm$^2$) by injecting an intracellular current of 80 μA/cm$^2$ (total injected current of 0.3 mA). Pacing cycle length (PCL) values were based on a mean AFCL ($AFCL_{mean}$) computed as an average on 4 electrograms located in septal area 316 around fossa ovalis 318 over 10 minutes of sustained AF. The septal pacing algorithm was generally composed of two phases including: 1) a rapid (overdrive) pacing phase at a PCL shorter than $AFCL_{mean}$ for 10 to 30 seconds, in order to capture the electrical activity of a substantial portion of both atria, and 2) a slow (underdrive) pacing phase at a PCL longer than $AFCL_{mean}$ during 1.5 seconds, in order to eliminate residual fibrillating wavelets that could survive in areas distant from the septum during the rapid pacing phase. An abrupt transition was applied between these two phases.

In the first phase of the AF pacing algorithm employed in the study, it was established that capture of both atria (bilateral capture) had to be established by rapid septal pacing. In order to select the PCL needed to achieve this bilateral capture, the capture window was first determined. PCLs were systematically tested in the range from 50% to 100% $AFCL_{mean}$ at 2% $AFCL_{mean}$ increments. The duration of each pacing episode was 30 seconds and capture results were averaged across the 40 initial conditions of the AF database (IC1 to IC40). The percentage of capture was computed as the percentage of time spent in bilateral capture during the total pacing sequence of 30 seconds. The capture window was defined as the range of PCL for which the percentage of time spent in bilateral capture was above 70%. Within this capture window, PCL values having stable capture results (standard deviation of the mean percentage of capture less than 5%) were retained for the test of the septal pacing algorithm employed in the study.

The assessment of atrial capture included computing electrograms in each atrium at four nodes located distant from the septum pacing site. During rapid pacing, a node was considered to be entrained if during at least five consecutive beats the measured cycle length was within ±3 milliseconds around the PCL. In each atrium separately, capture was achieved if at least three out of four nodes were entrained. Bilateral capture of the septum was achieved when both left and right atrium 300, 302, respectively, were captured simultaneously.

In the second phase of the AF pacing algorithm employed in the study, massive depolarization wavefronts over the whole atrial surface were needed to extinguish AF wavelets that could survive in areas distant from the septum during rapid pacing. The PCL parameters of the slow pacing phase were determined based on preliminary observations. After a test of various slow PCLs, the value of 180% $AFCL_{mean}$ was retained as the steady state slow PCL, since it was the shortest PCL providing uniform and massive depolarizations leading to capture of the all or most of the atrial tissue. However, the abrupt transition from the rapid PCL to 180% $AFCL_{mean}$ implied a first long pause in the atrial tissue during which it was possible for residual reentries in the appendages to reinitiate AF. To avoid this problem, the slow pacing phase at 180% $AFCL_{mean}$ was preceded by one single pacing pulse at 130% $AFCL_{mean}$. Thus, the AF termination algorithm employed in the study included: 1) an overdrive pacing phase at a PCL shorter than $AFCL_{mean}$ for 10 to 30 seconds, in order to capture the electrical activity of a substantial portion of both atria, 2) a first underdrive pacing phase at a PCL longer than $AFCL_{mean}$ for a single pacing pulse to inhibit or prevent residual reentries in the appendages to reinitiate AF, and 2) a second underdrive pacing phase also at a PCL longer than $AFCL_{mean}$ during 1.5 seconds, in order to eliminate residual fibrillating wavelets that could survive in areas distant from the septum during the rapid pacing phase. An abrupt transition was applied between these two phases.

The study protocol for the evaluation of the septal pacing algorithm included the following steps. For each initial condition of the AF database (IC1 to IC40), the rapid pacing phase was applied during a variable period of 10 to 30 seconds, followed by an abrupt transition to the slow pacing phase of 1.5 seconds. The transition from rapid to slow pacing was simulated at 50 different time instants (T1 to T50) of the rapid pacing phase, taken during the rapid pacing phase after 10 to 30 seconds, with 400 milliseconds increments. At the end of the slow pacing phase, the atrial tissue was allowed to evolve during another 0.5 seconds to assess AF termination. For each initial condition IC1 to IC40, the AF termination success rate was computed as an average from T1 to T50.

Results obtained with the proposed septal algorithm (rapid pacing phase followed by an abrupt transition to the slow pacing phase) were compared to results obtained when applying the rapid septal pacing phase only. Comparisons were done using Wilcoxon's rank sum test.

After 10 seconds of rapid pacing, capture was considered as stable, meaning that a periodic pattern was observed with a large portion of atrial tissue being controlled by the PCL (except for the reentrant wavelets still present in areas distant from the septum). This capture pattern could occasionally involve anchored waves rotating periodically around anatomical obstacles. It was hypothesized that the presence of these anchored waves could reduce the AF termination rates by sending wavelets back to the stimulation site during the transition between rapid and slow pacing. Therefore, for each capture pattern obtained after 10 seconds of rapid pacing of the AF database initial conditions (IC1 to IC40), a visual inspection was performed to count the number of anchored waves around the following major anatomical obstacles: tricuspid valve 304, superior and inferior vena cava 310, 312, respectively, coronary sinus 314, mitral valve 306 and pulmonary veins 308. The impact of this number of anchored waves on the AF termination rate for each AF initial condition was then assessed.

Figure 10A:
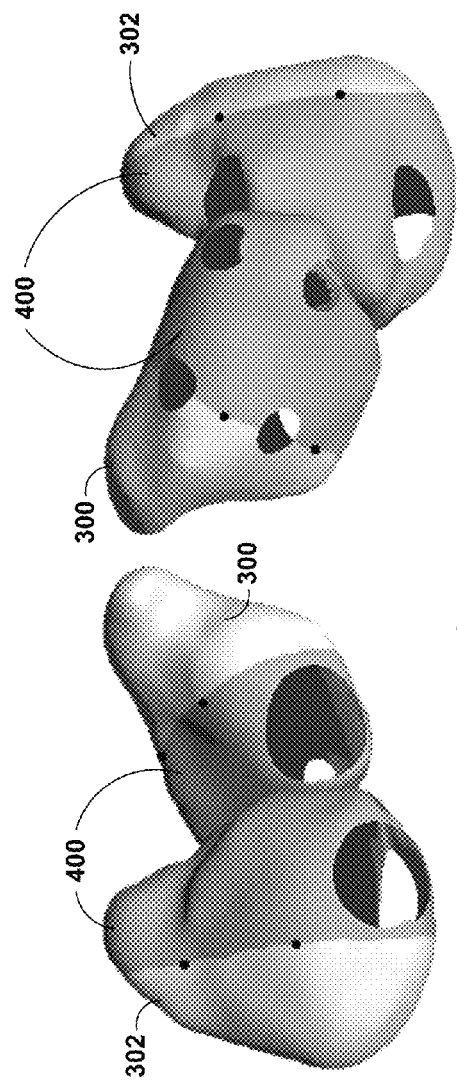
FIG. 10A is an image illustrating atrial tissue capture during overdrive pacing in the three-dimensional monolayer atrial geometric model employed in the study.
Figure 10B:
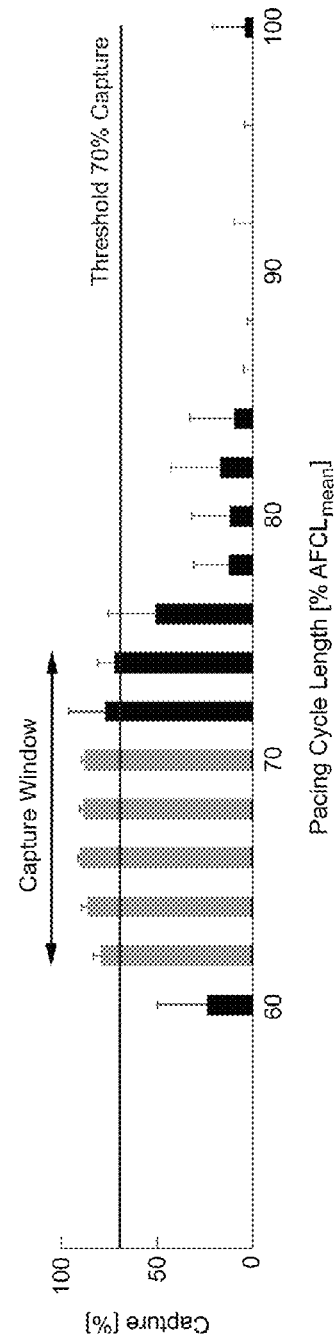
FIG. 10B is a histogram illustrating the atrial tissue capture window obtained for septal overdrive pacing in the study.

FIG. 10A is an image of the three-dimensional monolayer atrial geometric model of left and right atria 300, 302, respectively, of FIG. 9. In FIG. 10A, capture area 400 illustrates the portion of atrial tissue considered to automatically assess capture of left and right atria 300, 302, respectively. FIG. 10B is a histogram illustrating the capture window obtained for septal rapid pacing in the study. The capture window includes rapid pacing frequencies that result in a capture of the tissue of left and right atria 300, 302, respectively, during more than 70% of the total simulation time. In FIG. 10B, for an average $AFCL_{mean}$ equal to 99.76±25.20 milliseconds, the capture window was 62-74% $AFCL_{mean}$. Within this capture window, five PCL values were selected for the testing of the rapid pacing phase: 62%, 64%, 66%, 68%, and 70% $AFCL_{mean}$. These values were combined with PCL values of the slow pacing phase, i.e. 180% $AFCL_{mean}$ pacing preceded by one pacing pulse at 130% $AFCL_{mean}$, which resulted in a total of 10,000 simulations based on 5 PCL multiplied by 40 initial conditions multiplied by 50 time instants for the transition between rapid and slow pacing.

Figure 11:
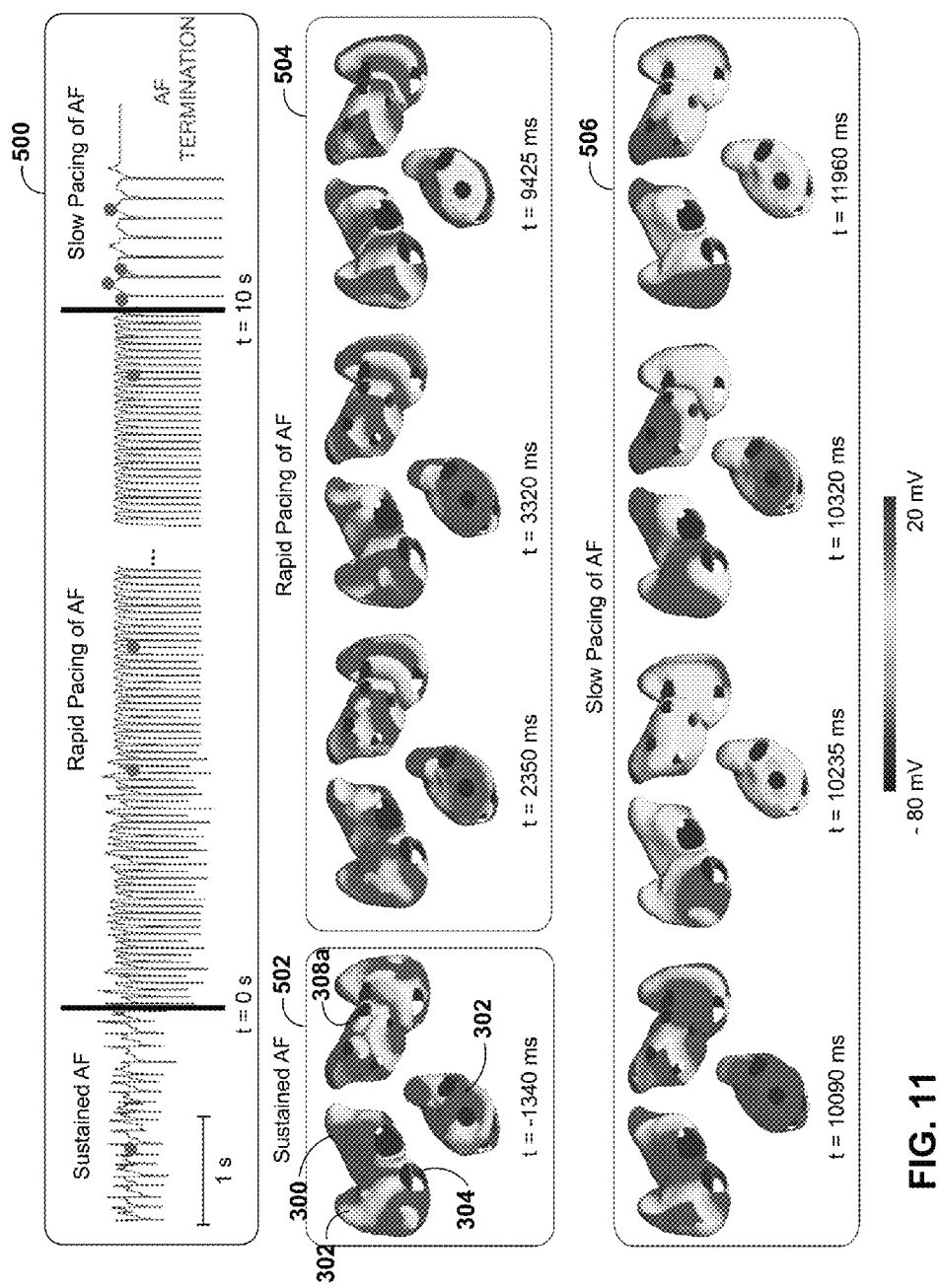
FIG. 11 includes an atrial electrogram output and several contour maps of the geometric model of the left and right atria during a successful AF termination employing a septal pacing algorithm in accordance with this disclosure.

FIG. 11 illustrates an example of a successful AF termination employing a septal pacing algorithm in accordance with this disclosure. FIG. 11 includes atrial electrogram 500 output during different phases of the example AF termination test and contour maps 502, 504, 506 of the geometric model of left and right atria 300, 302, respectively, during the period of sustained AF, overdrive pacing, and the first and the second underdrive pacing phases, respectively, of the septal pacing algorithm. The contour maps 502, 504, 506 represent electrical conduction through the cardiac tissue of left and right atria, 300, 302, respectively, during the different phases of the example of FIG. 11. The example simulation of FIG. 11 corresponds to IC2 and T1 for a rapid (overdrive) PCL of 64% of $AFCL_{mean}$ and a second slow (second underdrive) PCL of 180% of $AFCL_{mean}$ preceded with one pacing pulse at a first slow (first underdrive) PCL of 130% $AFCL_{mean}$.

In the example simulation of FIG. 11, during sustained AF, multiple reentrant wavelets were observed. Compared to normal sinus rhythm, APD was shorter and CV slower during AF (about 60 cm/s). During the rapid pacing phase at 64% $AFCL_{mean}$, a gradual capture of both atria 300, 302 was visible, starting in this case by a capture in the posterior of right atria 302 (t=2350 milliseconds), followed by the posterior of left atria 300 (t=3320 milliseconds: posterior left and right atria 300, 302, respectively captured), and finally by the anterior of left and right atria 300, 302, respectively. During this process, pace-induced wavefronts were fast enough to spread in both left and right atria 300, 302, respectively, gradually blocking AF reentries. In the example of FIG. 11, bilateral capture was achieved after 5 seconds of rapid pacing, with both left and right atria 300, 302, respectively, controlled at the rapid PCL, except for some residual reentries in the left atria appendage and the right atrial wall (t=9425 milliseconds). It was also observed that anchored waves around anatomical obstacles could be present during bilateral capture. In this case two anchored waves were present around tricuspid valve 304 and left superior pulmonary vein 308a.

The abrupt transition from rapid to the first slow pacing phase was applied after 10 seconds. The first slow pacing phase was applied for one pacing pulse at 130% $AFCL_{mean}$ and the second slow pacing phase was applied thereafter at 180% $AFCL_{mean}$. A longer period with no electrical activity was observed between the last rapid pacing pulse and the first slow pacing pulse, where the atrial tissue had time to repolarize (t=10090 milliseconds), implying a prolongation of APD and an increase in CV for the next wavefronts. Anchored waves could reenter the atrial tissue after its repolarization, but were stopped with the first slow pacing pulse before being able to propagate to the whole atria. The first slow pacing phase had a longer APD, leaving less space for the reentrant wavelets to be sustained, and this phenomenon was amplified by the increased CV of the reentries. At t=10235 milliseconds self-annihilation of the residual reentries were observed due to the presence of the first slow pacing phase wave. In the example of FIG. 11, all reentrant waves could be stopped by the first slow pacing phase (t=10320 milliseconds: repolarization of the first slow pacing phase pulse after annihilation of all residual reentries) and the second and subsequent slow pacing phase at 180% AFCL$_{mean}$ could take control of both left and right atria 300, 302, respectively, at a reduced cycle length (t=10960 milliseconds). In other simulations, more than one pacing pulse in the first slow pacing phase was needed to annihilate all reentrant waves and subsequently control left and right atria 300, 302, respectively.

Figure 12:
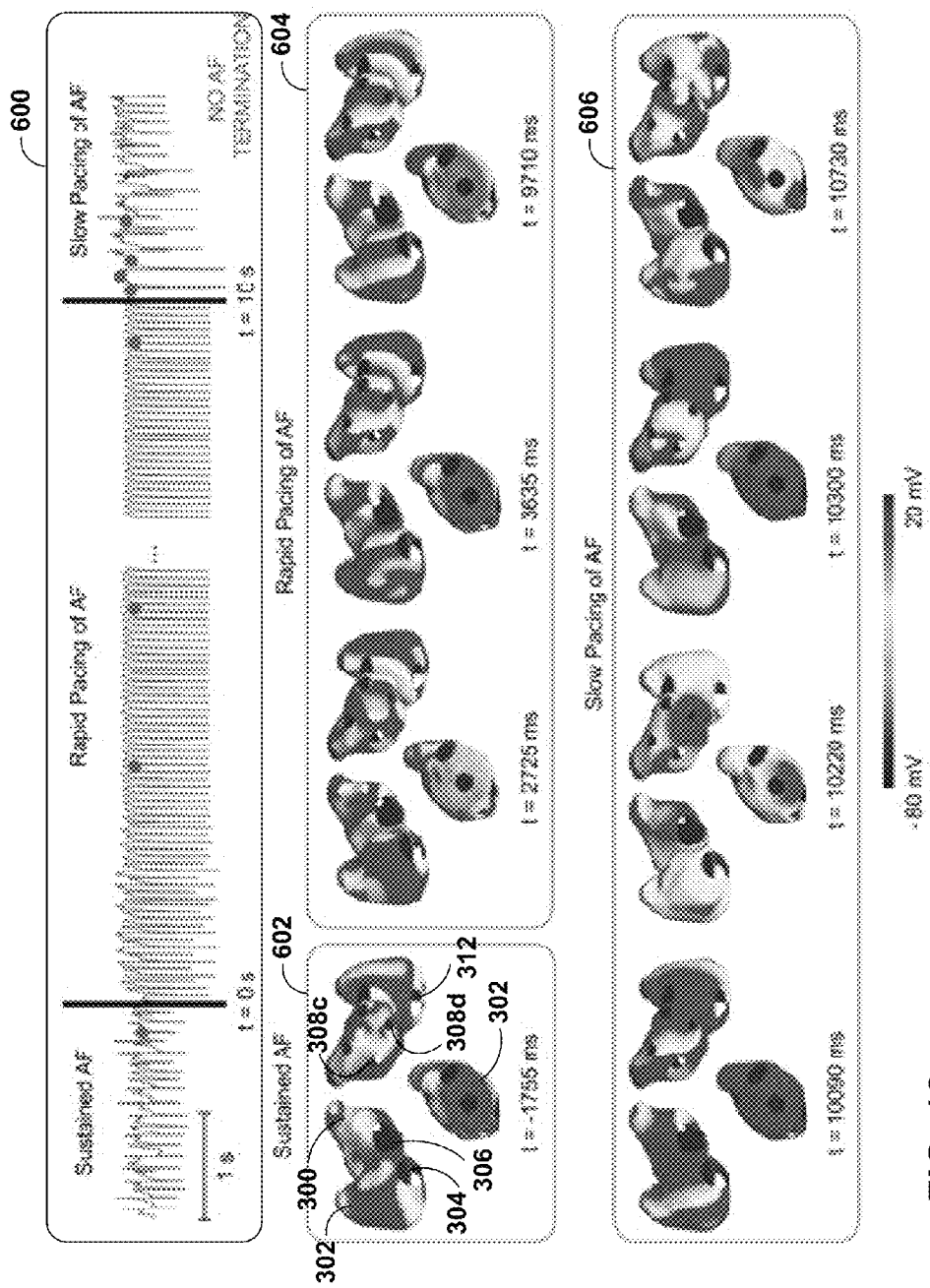
FIG. 12 includes an atrial electrogram output and several contour maps of the geometric model of the left and right atria during an unsuccessful AF termination employing a septal pacing algorithm in accordance with this disclosure.

FIG. 12 illustrates an example of an unsuccessful AF termination employing a septal pacing algorithm in accordance with this disclosure. FIG. 12 includes atrial electrogram 600 output during different phases of the example AF termination test and contour maps 602, 604, 606 of the geometric model of left and right atria 300, 302, respectively, during the period of sustained AF, overdrive pacing, and the first and the second underdrive pacing phases, respectively, of the septal pacing algorithm. The contour maps 602, 604, 606 represent electrical conduction through the cardiac tissue of left and right atria, 300, 302, respectively, during the different phases of the example of FIG. 12. The example simulation of FIG. 12 corresponds to IC28 and T1 for a rapid (overdrive) PCL of 64% of AFCL$_{mean}$ and a second slow (second underdrive) PCL of 180% of AFCL$_{mean}$ preceded with one pacing pulse at a first slow (first underdrive) PCL of 130% AFCL$_{mean}$.

FIG. 12 presents an example in which the septal pacing algorithm did not succeed in terminating AF using the same rapid and slow PCL as in the example simulation of FIG. 11, but started on a different AF initial condition (IC28 in FIG. 12 versus IC2 in FIG. 11). The establishment of the bilateral capture pattern was similar to what has been observed in the simulation of FIG. 11, starting with a progressive control of the anterior of left atrium 300 and the posterior of right atrium 302 (t=2725 milliseconds and t=3635 milliseconds, respectively). However, the final capture state was different, with a higher number of anchored waves. In this case five anchored waves were present around tricuspid valve 304, inferior vena cava 312, mitral valve 306 and right and left inferior pulmonary veins 308c, 308d (t=9710 milliseconds). The abrupt transition from rapid to the first slow pacing phase was applied after 10 seconds. The longer period with no electrical activity between the last rapid pacing pulse and the first slow pacing pulse at 130% AFCL$_{mean}$, during which the atrial tissue had time to repolarize, was also observed (t=10090 milliseconds). However, the first slow pacing pulse could only take control of right atrium 302 but could not stop the anchored waves from reentering the atrial tissue in the appendage of left atrium 300 and around left inferior pulmonary vein 308d (t=10220 milliseconds). During the repolarization of right atrium 302, these reentries could gradually invade the anterior and posterior left atrium 300 (t=10300 milliseconds: just before the application of the second slow pacing phase at 180% AFCL$_{mean}$). AF could then also spread to right atrium 302 even in the presence of the 180% AFCL$_{mean}$ second slow pacing phase, which was unable to capture the atria (t=10730 milliseconds).

AF termination results from the study described above are summarized in Table 1 for rapid (overdrive) pacing only and for the proposed septal pacing algorithm combining rapid (overdrive) and slow (underdrive) pacing. It was identified that the combination leading to the highest AF termination rate of 29% was a rapid pacing at 64% AFCL$_{mean}$ during 10-30 seconds followed by an abrupt transition to a first slow pacing phase at first frequency of 130% AFCL$_{mean}$ for one pacing pulse and then a second slow pacing phase at a second frequency of 180% AFCL$_{mean}$ during 1.5 seconds. Using a rapid PCL different from 64% AFCL$_{mean}$ changed the bilateral capture pattern obtained before the transition to the first slow pacing phase and decreased the average AF termination rate as the PCL was moved away from the optimum.

TABLE 1

| | Rapid Pacing Length (% AFCL$_{mean}$) | | | | | Average |
|---|---|---|---|---|---|---|
| | 62 | 64 | 66 | 68 | 70 | (62-70) |
| Rapid (overdrive) pacing only | 8.8% | 21.2% | 11.5% | 3.4% | 6.0% | 10.2% |
| Rapid + slow (underdrive) pacing | 20.9% | 29.0% | 24.2% | 15.9% | 11.2% | 20.2% |

Figure 13:
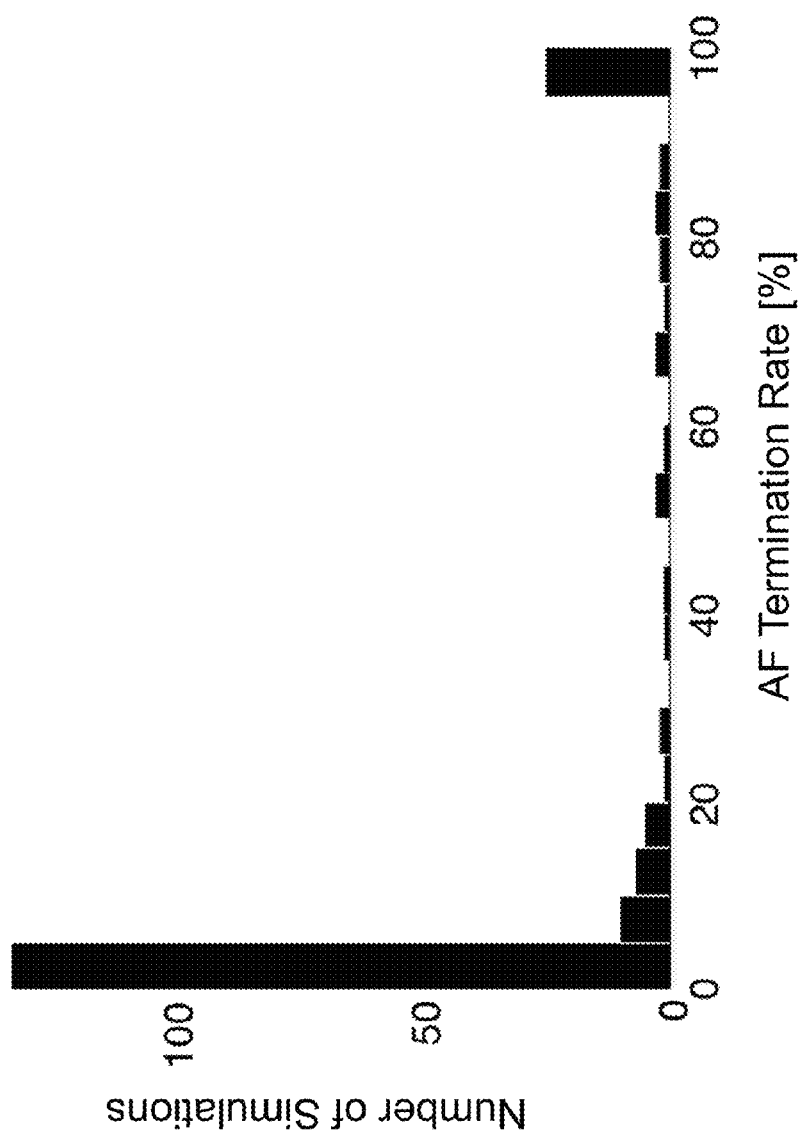
FIG. 13 is a histogram of the AF termination rates considering all overdrive pacing cycle lengths included in the study taken together.

A histogram of the AF termination rates considering all rapid PCLs included in the study taken together is shown in FIG. 13. Most AF initial conditions (77.5%) led to an AF termination rate between 0-20%. A smaller number of initial conditions (15.5%) led to an AF termination rate in the range 80-100%, while very few initial conditions (7%) led to an AF termination rate in the range 20-80%.

Compared to the case where only rapid septal pacing was applied, the septal pacing algorithm employed in the study could, in most cases, double the AF termination rate. When considering the average performance of the pacing scheme over the 5 rapid PCL tested, the addition of the slow pacing phase provided a significant increase of the AF termination rate from 10.2% to 20.2%. This AF termination rate increase corresponded to a Wilcoxon rank sum test p-value of less than 0.05, which may be used as a measure of the statistical significance of the improvement observed with versus without underdrive pacing.

Analysis of the simulations run as part of the study revealed that the configuration of the capture pattern obtained at the end of the rapid pacing phase was an important factor in determining the success of the septal pacing algorithm. The time needed to achieve bilateral capture varied from one simulation to the other. However, it was observed that 10 seconds was a satisfactory pacing duration to obtain a stabilized bilateral capture pattern in all or most cases. For the 40 AF initial conditions and the 5 PCL tested in the rapid pacing phase (N=200), the number and the location of the anchored waves present in the bilateral capture pattern achieved after 10 seconds of rapid pacing were documented. The percentage of occurrence of anchored waves on each anatomical obstacle was the following: tricuspid valve: 51%, superior vena cava: 44.5%, inferior vena cava: 53%, coronary sinus: 39.5%, mitral valve: 54%, left superior pulmonary vein: 45%, left inferior pulmonary vein: 38.5%, right superior pulmonary vein: 36.5%, right inferior pulmonary vein: 44%. Therefore, there was no preferential site for the anchoring during the rapid pacing phase. In average, 4.1±1.4 anchored waves were observed in the stabilized capture patterns.

The effect of the presence and the location of the anchored waves on the subsequent AF termination rate were also analyzed. On average, when considering each anchoring site separately, the AF termination rate with a specific anchoring was 14.21% and increased to 24.95% when the anchoring was not present. A significant difference was observed on the AF termination rate with and without the anchored wave for the following locations: inferior vena cava, coronary sinus, mitral valve and all pulmonary veins except the right superior pulmonary vein. An extreme case was observed at the coronary sinus location where the AF termination rate without the anchoring was 31.2% and dropped to 3.4% when the anchoring was present.

Figure 14:
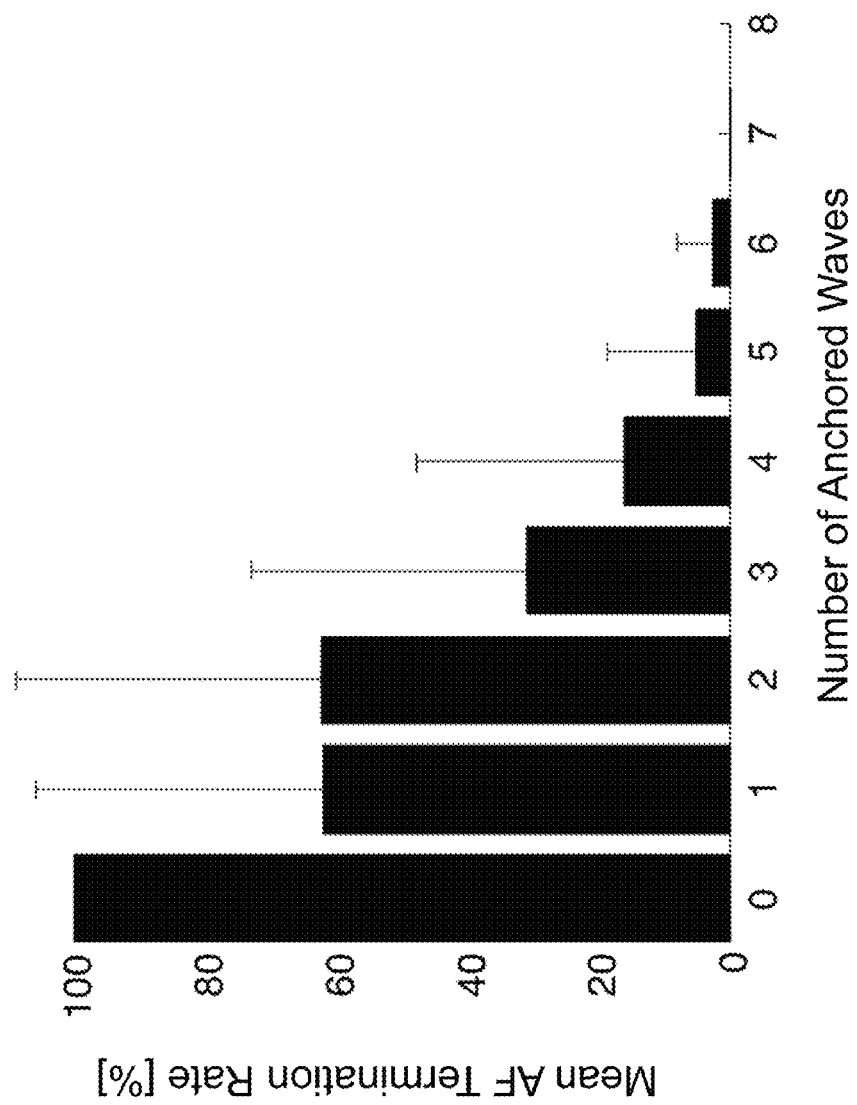
FIG. 14 is a histogram illustrating the effect of the number of anchored waves on the AF termination rate.

Finally the effect of the number of anchored waves on the AF termination rate was assessed and is illustrated in the histogram of FIG. 14. It was observed that higher termination rates were consistently linked to a low number of anchored waves, and vice versa. Based on these results, four anchored waves appears to be an important number with respect to AF termination. If the number of anchored waves was higher or equal to four, the average termination rate was 9.2±23.4%. If the number of anchored waves was lower than four, the average termination rate was 40.7±44.9%. A significant difference was observed between these two groups (Wilcoxon rank sum test p-value of less than 10-7).

Various examples of the invention have been described. These and other examples are within the scope of the following claims.

The invention claimed is:

1. A method for terminating a tachyarrhythmia comprising:
   detecting the tachyarrhythmia;
   determining a cycle length of the detected tachyarrhythmia;
   delivering overdrive pacing to a septum of a heart of a patient in response to the detection;
   delivering a first underdrive pacing to the septum at a first frequency; and
   delivering a second underdrive pacing to the septum at a second frequency, wherein at least one of a frequency of the overdrive pacing, the first frequency of the first underdrive pacing, or the second frequency of the second underdrive pacing is a function of the cycle length of the tachyarrhythmia.

2. The method of claim 1, wherein an interval between the delivery of the overdrive pacing and the delivery of the first underdrive pacing is less than approximately 300 milliseconds.

3. The method of claim 1, wherein the overdrive pacing and the first and second underdrive pacing are delivered via a plurality of electrodes arranged symmetrically on the septum.

4. The method of claim 3, wherein the electrodes are arranged symmetrically on one of an atrial or a ventricular septum of the heart of the patient.

5. The method of claim 4, wherein the electrodes comprises a plurality of electrodes arranged in a ring on the septum.

6. The method of claim 5, wherein the ring of electrodes is arranged around an atrial septum ring on the atrial septum.

7. The method of claim 5, wherein the ring of electrodes is arranged on a fossa ovalis in the atrial septum.

8. The method of claim 4, wherein the electrodes are arranged symmetrically about a fossa ovalis in the atrial septum.

9. The method of claim 4, wherein the electrodes comprise an array of electrodes arranged on the septum.

10. The method of claim 1, wherein overdrive pacing is delivered at a frequency in a range from approximately 62% to approximately 74% of the cycle length of the tachyarrhythmia.

11. The method of claim 1, wherein the first frequency of the first underdrive pacing is approximately equal to 130% of the cycle length of the tachyarrhythmia.

12. The method of claim 1, wherein the second frequency of the second underdrive pacing is approximately equal to 180% of the cycle length of the tachyarrhythmia.

13. The method of claim 1, wherein a duration of at least one of the overdrive pacing, the first underdrive pacing, or the second underdrive pacing is predetermined.

14. The method of claim 1, wherein the tachyarrhythmia is one of an atrial or a ventricular fibrillation.

15. The method of claim 14, further comprising sensing atrial activity during the delivery of overdrive pacing, wherein delivering the overdrive pacing comprises delivering the overdrive pacing until the atrial activity indicates that the atria of the heart are substantially captured by the overdrive pacing.

16. The method of claim 14, further comprising sensing ventricular activity during the delivery of overdrive pacing, wherein delivering the overdrive pacing comprises delivering the overdrive pacing until the ventricular activity indicates that the ventricles of the heart are substantially captured by the overdrive pacing.

17. The method of claim 1, wherein delivering the first underdrive pacing comprises delivering one pacing pulse at the first frequency.

18. The method of claim 1 further comprising stopping delivery of the overdrive pacing before delivering the first underdrive pacing.

19. The method of claim 1 further comprising stopping delivery of the first underdrive pacing before delivering the second underdrive pacing.

* * * * *